(12) United States Patent
Williams et al.

(10) Patent No.: US 7,563,619 B2
(45) Date of Patent: Jul. 21, 2009

(54) MAMMARY STEM CELL MARKER

(75) Inventors: Bart Williams, Grand Rapids, MI (US); Caroline M. Alexander, Madison, WI (US); Charlotta Lindvall, Grand Rapids, MI (US); Nisha McConnell, Madison, WI (US)

(73) Assignees: Van Andel Research Institute, Grand Rapids, MI (US); Wisconsin Alumni Research Foundation, Madison, WI (US)

( * ) Notice: Subject to any disclaimer, the term of this patent is extended or adjusted under 35 U.S.C. 154(b) by 56 days.

(21) Appl. No.: 11/807,937

(22) Filed: May 30, 2007

(65) Prior Publication Data

US 2007/0280948 A1  Dec. 6, 2007

Related U.S. Application Data

(60) Provisional application No. 60/809,281, filed on May 30, 2006.

(51) Int. Cl.
*C12N 5/00* (2006.01)
*C12N 15/00* (2006.01)

(52) U.S. Cl. ........................... 435/455; 435/325

(58) Field of Classification Search .................. 435/455, 435/325
See application file for complete search history.

(56) References Cited

U.S. PATENT DOCUMENTS

2005/0089518 A1  4/2005  Clarke et al.
2006/0281137 A1  12/2006  Stingl et al.

FOREIGN PATENT DOCUMENTS

WO  WO 2006/055635 A  5/2006

OTHER PUBLICATIONS

Lindvall (Stem Cell Rev. 2007, vol. 3, p. 157-168).*
Lindvall, et al., The Wnt signaling receptor Lrp5 is required for mammary ductal stem cell activity and wnt1-induced tumorigenesis. J. Biol. Chem. (2006) 281(46): 35081-35087.
Li, et al., Evidence that transgenes encoding components of the Wnt signaling pathway preferentially induce mammary cancers from progenitor cells. Proc. Nat. Ac. of Sci. USA (2003) 100(26): 15853-15858.
Paguirigan, A., Beebe, D. J., Liu, B., and Alexander, C., Mammary Stem and Progenitor Cells: Tumour Precursors? (2006) Eur. J. Cancer 42, 1225-1236.
Al-Hajj, M., Wicha, M. S., Benito-Hernandez, A., Morrison, S. J. & Clarke, M. F. Prospective identification of tumorigenic breast cancer cells. Proc. Natl Acad. Sci. USA 100, 3983-3988 (2003).
Woodward, Wendy A., et al: "On Mammary Stem Cells" (2005) Journal of cell Science (118) 16:3585-3594.
Shackelton, Mark, et al: "Generation of a Functional Mammary Gland from a Single Stem Cell" (2006) Nature (London), (439)7072:84-88.
Lindeman, Geoffrey J., et al: "Shedding Light on mammary Stem cells and Tumorigenesis" (2006) Cell Cycle, (5)7:671-672.
Stingl, John, et al: "Purification and Unique Properties of Mammary Epithelial Stem Cells" (2006) Nature (London), (439)7079:993-997.
Chu, Emily Y, et al: "Canonical WNT Signaling Promotes Mammary Placode Development and is Essential . . . " (2004) Development (Cambridge), (131)19:4819-4929.
Liu, Bob Y, et al: "The Transforming Activity of Wnt Effectors Correlates with their Ability . . . " (2004) Proceedings of the Natl Acad. of Sciences of USA, (101)12:4158-4163.
Giambernardi, Troy A., et al: "Role of Lrp5 in Mammary Development and MMTV-Wnt1 . . . " (2003) Proc. of the Amer. Assoc. for Cancer Research, (44):991-992.
Van't Veer, Laura J., et al: "Gene Expression Profiling Predicts Clinical Outcome of Breast Cancer" (2002) Nature (London), (415)6871:530-536.
Young, John J., et al: "LRP5 and LRP6 are Not Required for Protective Antigen-Mediated . . . " (2007) Plos Pathogens, (3)3:00001-00009.
Lindvall, Charlotta, et al: "Wnt Signaling Stem Cells and the cellular Origin of Breast Cancer" (2007) Stem Cell Reviews, (3)2:157-168.

* cited by examiner

*Primary Examiner*—Michael C. Wilson
(74) *Attorney, Agent, or Firm*—Quarles & Brady LLP

(57) ABSTRACT

It is disclosed here that low density lipoprotein receptor-related protein 5 (LRP5) is a cell surface marker for somatic mammary stem cells and mammary tumor stem cells. The disclosure here provides new tools for enriching somatic mammary stem cells and mammary tumor stem cells. Methods of screening for agents that modulate LRP5 activity, of treating mammary tumor or breast cancer, of monitoring somatic mammary stem cells and mammary tumor stem cells in vivo are also provided, and of assessing prognosis of human breast cancer.

12 Claims, 9 Drawing Sheets
(3 of 9 Drawing Sheet(s) Filed in Color)

FIG. 3
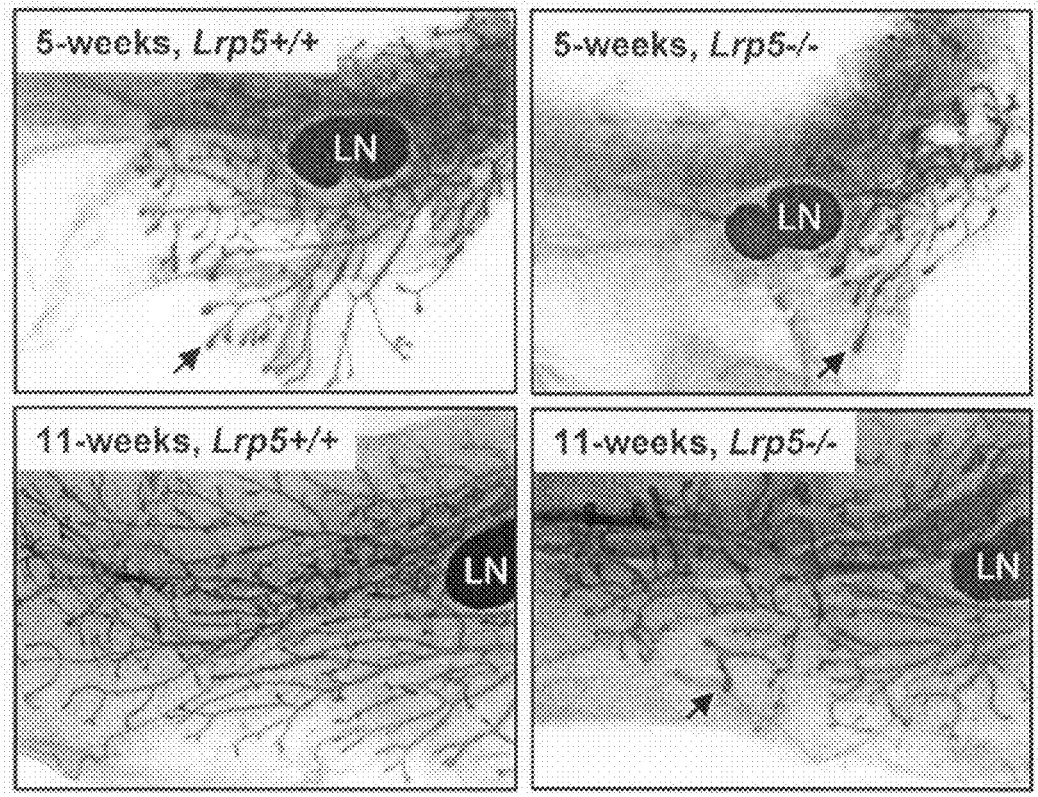
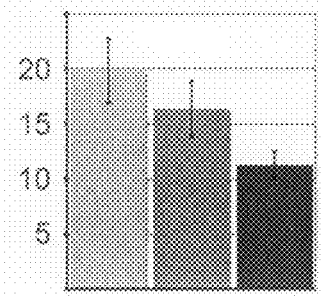
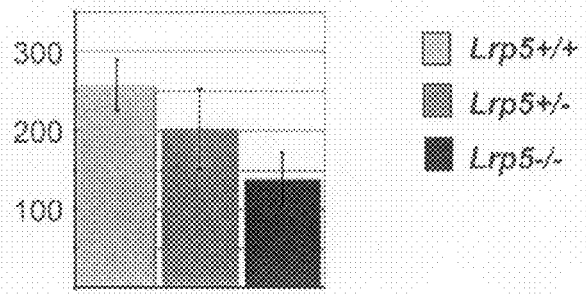

FIG. 4
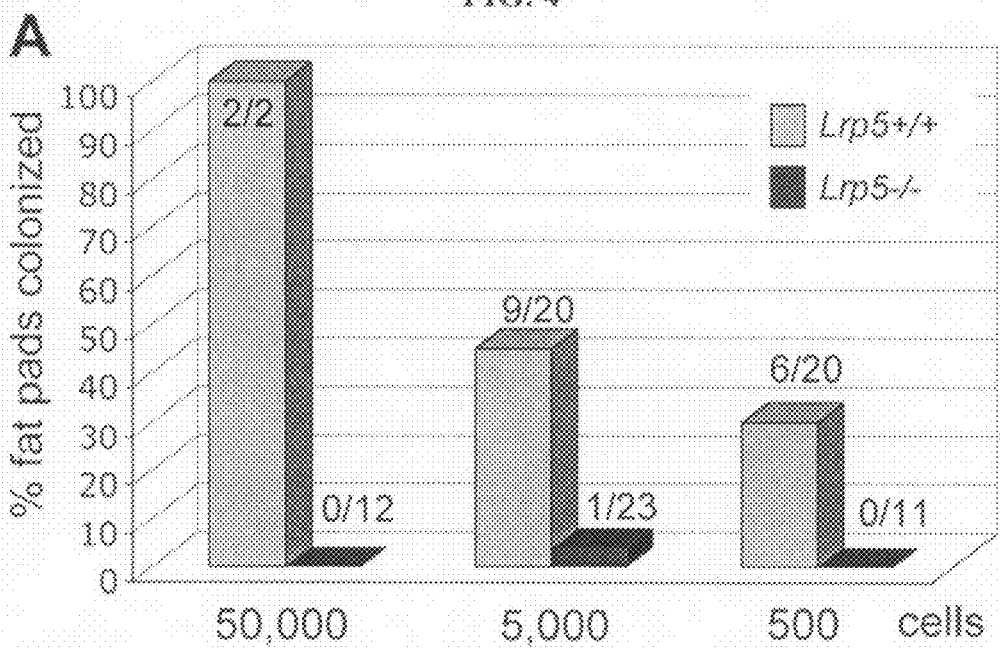
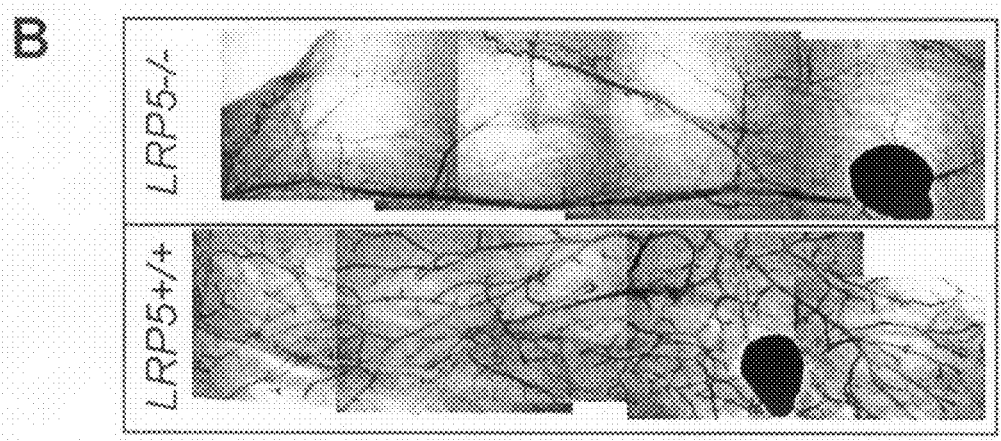

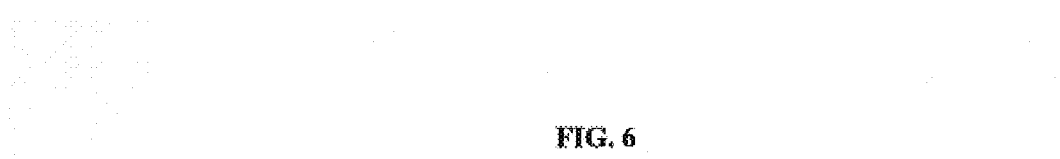
FIG. 6
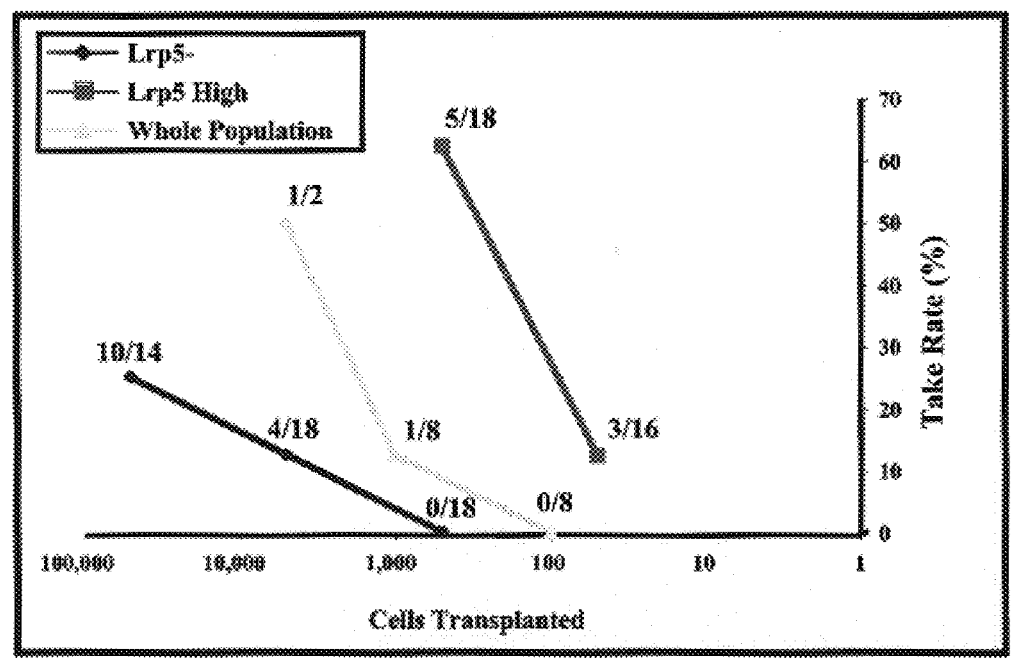

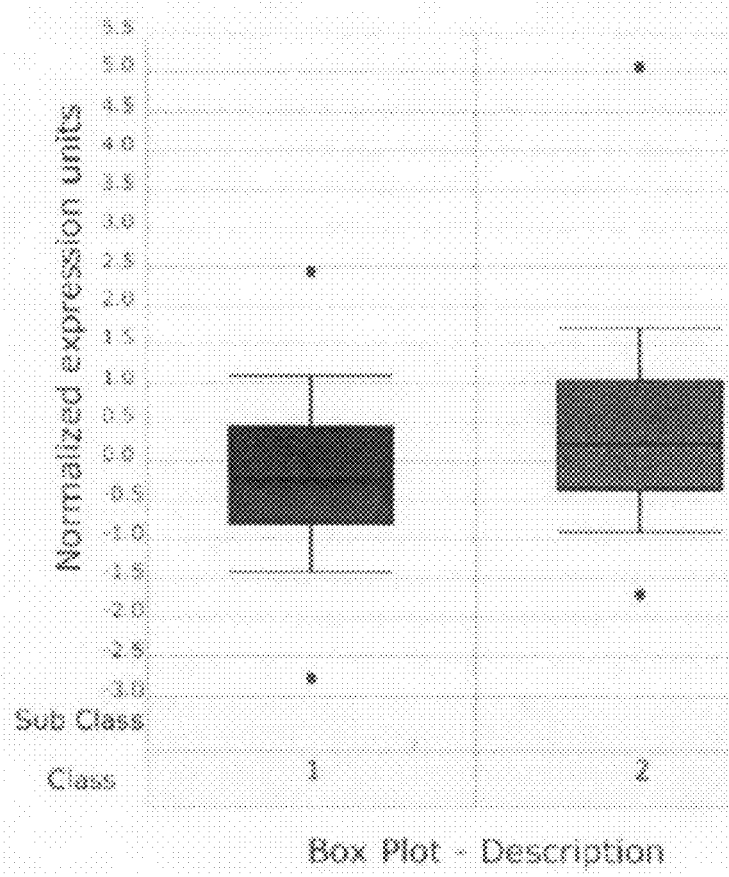

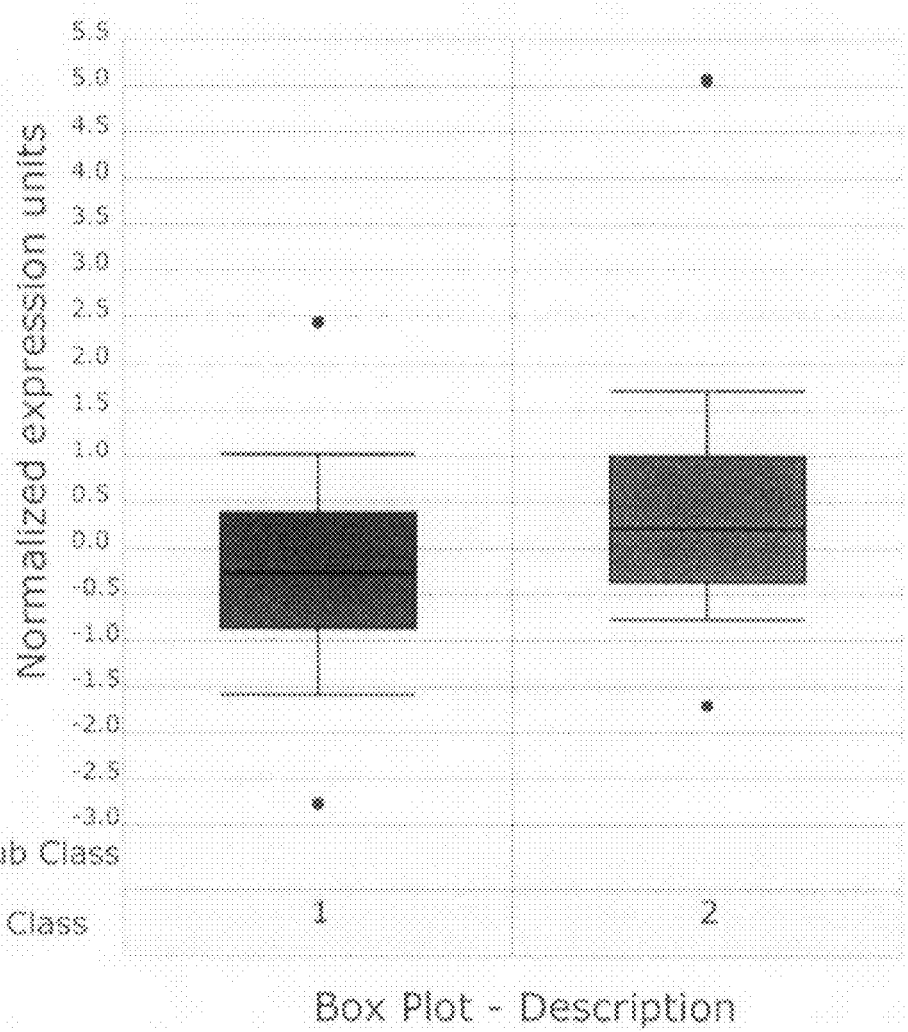

SEQUENCE LISTING

<160> NUMBER OF SEQ ID NOS: 4

<210> SEQ ID NO 1
<211> LENGTH: 5224
<212> TYPE: DNA
<213> ORGANISM: homo sapiens

<400> SEQUENCE: 1

```
atgggggccg tcctgaggag cctcctggcc tgcagcttct gtgtgctcct gagagcggcc      60
cctttgttgc tttatgcaaa cagacgggac ttgcgattgg ttgatgctac aaatggcaaa     120
gagaatgcta cgattgtagt tggaggcttg gaggatgcag ctgcggtgga ctttgtgttt     180
agtcatggct tgatatactg gagtgatgtc agcgaagaag ccattaaacg aacagaattt     240
```

```
aacaaaactg agagtgtgca gaatgttgtt gtttctggat tattgtcccc cgatgggctg    300
gcatgtgatt ggcttggaga aaaattgtac tggacagatt ctgaaactaa tcggattgaa    360
gtttctaatt tagatggatc tttacgaaaa gttttatttt ggcaagagtt ggatcaaccc    420
agagctattg ccttagatcc ttcaagtggg ttcatgtact ggacagactg gggagaagtg    480
ccaaagatag aacgtgctgg aatggatggt tcaagtcgct tcattataat aaacagtgaa    540
atttactggc caaatggact gactttggat tatgaagaac aaaagcttta ttgggcagat    600
gcaaaactta atttcatcca caaatcaaat ctggatggaa caaatcggca ggcagtggtt    660
aaaggttccc ttccacatcc ttttgccttg acgttatttg aggacatatt gtactggact    720
gactggagca cacactccat tttggcttgc aacaagtata ctggtgaggg tctgcgtgaa    780
atccattctg acatcttctc tcccatggat atacatgcct tcagccaaca gaggcagcca    840
aatgccacaa atccatgtgg aattgacaat gggggttgtt cccatttgtg tttgatgtct    900
ccagtcaagc ctttttatca gtgtgcttgc cccactgggg tcaaactcct ggagaatgga    960
aaaacctgca agatggtgc cacagaatta ttgctttag ctcgaaggac agacttgaga    1020
cgcatttctt tggatacacc agattttaca gacattgttc tgcagttaga agacatccgt    1080
catgccattg ccatagatta cgatcctgtg aaggctaca tctactggac tgatgatgaa    1140
gtgagggcca tacgccgttc atttatagat ggatctggca gtcagtttgt ggtcactgct    1200
caaattgccc atcctgatgg tattgctgtg actgggttg cacgaaatct ttattggaca    1260
gacactggca ctgatcgaat agaagtgaca aggctcaatg ggaccatgag gaagatcttg    1320
atttcagagg acttagagga accccgggct attgtgttag atcccatggt tgggtacatg    1380
tattggactg ctggggagaa aattccgaaa attgagcgag cagctctgga tggttctgac    1440
cgtgtagtat tggttaacac ttctcttggt tggccaaatg gtttagcctt ggattatgat    1500
gaaggcaaaa tatactgggg agatgccaaa acagacaaga ttgaggttat gaatactgat    1560
ggcactggga gacgagtact agtggaagac aaaattcctc acatatttgg atttactttg    1620
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgttttc acggagagca    1920
gatatcagac gaatttctct ggaaacaaac aataataatg tggctattcc actcactggt    1980
gtcaaagaag cttctgcttt ggattttgat gtgacagaca accgaattta ttggactgat    2040
atatcactca agaccatcag cagagccttt atgaatggca gtgcactgga acatgtggta    2100
gaattcggct tagattatcc agaaggcatg cagtagact ggcttgggaa gaacttgtac    2160
tgggcagaca caggaacgaa tcgaattgag gtgtcaaagt tggatgggca gcaccgacaa    2220
gttttggtgt ggaaagacct agatagtccc agagctctcg cgttggaccc tgccgaagga    2280
tttatgtatt ggactgaatg gggtggaaaa cctaagatag acagagctgc aatggatgga    2340
agtgaacgta ctaccttagt tccaaatgtg gggcggcaa acggcctaac tattgattat    2400
gctaaaagga ggctttattg gacagacctg gacaccaact aatagaatc ttcaaatatg    2460
cttgggctca accgtgaagt tatagcagat gacttgcctc atccttttgg cttaactcag    2520
taccaagatt atatctactg gacggactgg agccgacgca gcattgagcg tgccaacaaa    2580
```

```
accagtggcc aaaaccgcac catcattcag ggccatttgg attatgtgat ggacatcctc    2640
gtctttcact catctcgaca gtcagggtgg aatgaatgtg cttccagcaa tgggcactgc    2700
tcccacctct gcttggctgt gccagttggg ggttttgttt gtggatgccc tgcccactac    2760
tctcttaatg ctgacaacag gacttgtagt gctcctacga cttttcctgct cttcagtcaa    2820
aagagtgcca tcaaccgcat ggtgattgat gaacaacaga gccccgacat catccttccc    2880
atccacagcc ttcggaatgt ccgggccatt gactatgacc cactggacaa gcaactctat    2940
tggattgact cacgacaaaa catgatccga aaggcacaag aagatggcag ccagggcttt    3000
actgtggttg tgagctcagt tccgagtcag aacctggaaa tacaacccta tgacctcagc    3060
attgatattt acagccgcta catctactgg acttgtgagg ctaccaatgt cattaatgtg    3120
acaagattag atgggagatc agttggagtg gtgctgaaag gcgagcagga cagacctcga    3180
gccattgtgg taaacccaga gaaagggtat atgtattta ccaatcttca ggaaaggtct    3240
cctaaaattg aacgggctgc tttgatggg acagaacggg aggtcctctt tttcagtggc    3300
ttaagtaaac caattgcttt agcccttgat agcaggctgg gcaagctctt tgggctgat    3360
tcagatctcc ggcgaattga aagcagtgat ctctcaggtg ctaaccggat agtattagaa    3420
gactccaata tcttgcagcc tgtgggactt actgtgtttg aaaactggct ctattggatt    3480
gataaacagc agcaaatgat tgaaaaaatt gacatgacag gtcgagaggg tagaaccaaa    3540
gtccaagctc gaattgccca gcttagtgac attcatgcag taaaggagct gaaccttcaa    3600
gaatacagac agcaccctg tgctcaggat aatggtggct gttcacatat ttgtcttgta    3660
aaggggatg gtactacaag gtgttcttgc cccatgcacc tggttctact tcaagatgag    3720
ctatcatgtg gagaacctcc aacatgttct cctcagcagt ttacttgttt cacggggggaa    3780
attgactgta tccctgtggc ttggcggtgc gatgggttta ctgaatgtga agaccacagt    3840
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgcttttgttt aattgatcag ttccgctgtg ccaatggtca gtgcattgga    4020
aagcacaaga agtgtgatca taatgtggat tgcagtgaca agtcagatga actggattgt    4080
tatccgactg aagaaccagc accacaggcc accaatacag ttggttctgt tattggcgta    4140
attgtcacca ttttttgtgtc tggaactgta tactttatct gccagaggat gttgtgtcca    4200
cgtatgaagg gagatgggga aactatgact aatgactatg tagttcatgg accagcttct    4260
gtgcctcttg gttatgtgcc acacccaagt tctttgtcag gatctcttcc aggaatgtct    4320
cgaggtaaat caatgatcag ctccctcagt atcatggggg gaagcagtgg acccccctat    4380
gaccgagccc atgttacagg agcatcatca agtagttctt caagcaccaa aggcacttac    4440
ttccctgcaa ttttgaaccc tccaccatcc ccagccacag agcgatcaca ttacactatg    4500
gaatttggat attcttcaaa cagtccttcc actcataggt catacagcta caggccatat    4560
agctaccggc actttgcacc ccccaccaca ccctgcagca cagatgtttg tgacagtgac    4620
tatgctccta gtcggagaat gacctcagtg gcaacagcca aggctatac cagtgacttg    4680
aactatgatt cagaacctgt gccccacct cccacacccc gaagccaata cttgtcagca    4740
gaggagaact atgaaagctg cccaccttct ccatacacag agaggagcta ttctcatcac    4800
ctctacccac cgccaccctc tccctgtaca gactcctcct gaggagggggc cctcctcctc    4860
tgactgcctc caacgtaaaa atgtaaatat aaatttggtt gagatctgga ggggggagg    4920
gagctattag agaaggatga ggcagaccat gtacagttaa aattataaaa tggggtaggg    4980
```

```
aatactggag atatttgtac agaagaaaag gatatttata tattttctta aaacagcaga    5040
tttgctgctt gtgccataaa agtttgtata aaaaaaattt gtactaaaag tttattttt     5100 gcaaactaaa tacacaaagc atgccttaaa cccagtgaag caactgagta caaaggaaac    5160
aggaataata aaggcatcac tgaccaggaa tatctgggct ttattgatac caaaaaaaaa    5220
aaaa                                                                  5224

<210> SEQ ID NO 2
<211> LENGTH: 1615
<212> TYPE: PRT
<213> ORGANISM: homo sapiens

<400> SEQUENCE: 2

Met Glu Ala Ala Pro Gly Pro Pro Trp Pro Leu Leu Leu Leu
1               5                   10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285

Gln Glu Arg Gln Pro Phe Phe His Thr Arg Cys Glu Glu Asp Asn Gly
    290                 295                 300

Gly Cys Ser His Leu Cys Leu Leu Ser Pro Ser Glu Pro Phe Tyr Thr
305                 310                 315                 320
```

```
Cys Ala Cys Pro Thr Gly Val Gln Leu Gln Asp Asn Gly Arg Thr Cys
                325                 330                 335

Lys Ala Gly Ala Glu Glu Val Leu Leu Leu Ala Arg Arg Thr Asp Leu
                340                 345                 350

Arg Arg Ile Ser Leu Asp Thr Pro Asp Phe Thr Asp Ile Val Leu Gln
                355                 360                 365

Val Asp Asp Ile Arg His Ala Ile Ala Ile Asp Tyr Asp Pro Leu Glu
            370                 375                 380

Gly Tyr Val Tyr Trp Thr Asp Asp Glu Val Arg Ala Ile Arg Arg Ala
385                 390                 395                 400

Tyr Leu Asp Gly Ser Gly Ala Gln Thr Leu Val Asn Thr Glu Ile Asn
                    405                 410                 415

Asp Pro Asp Gly Ile Ala Val Asp Trp Val Ala Arg Asn Leu Tyr Trp
                420                 425                 430

Thr Asp Thr Gly Thr Asp Arg Ile Glu Val Thr Arg Leu Asn Gly Thr
            435                 440                 445

Ser Arg Lys Ile Leu Val Ser Glu Asp Leu Asp Glu Pro Arg Ala Ile
        450                 455                 460

Ala Leu His Pro Val Met Gly Leu Met Tyr Trp Thr Asp Trp Gly Glu
465                 470                 475                 480

Asn Pro Lys Ile Glu Cys Ala Asn Leu Asp Gly Gln Glu Arg Arg Val
                    485                 490                 495

Leu Val Asn Ala Ser Leu Gly Trp Pro Asn Gly Leu Ala Leu Asp Leu
                500                 505                 510

Gln Glu Gly Lys Leu Tyr Trp Gly Asp Ala Lys Thr Asp Lys Ile Glu
            515                 520                 525

Val Ile Asn Val Asp Gly Thr Lys Arg Arg Thr Leu Leu Glu Asp Lys
        530                 535                 540

Leu Pro His Ile Phe Gly Phe Thr Leu Leu Gly Asp Phe Ile Tyr Trp
545                 550                 555                 560

Thr Asp Trp Gln Arg Arg Ser Ile Glu Arg Val His Lys Val Lys Ala
                    565                 570                 575

Ser Arg Asp Val Ile Ile Asp Gln Leu Pro Asp Leu Met Gly Leu Lys
                580                 585                 590

Ala Val Asn Val Ala Lys Val Val Gly Thr Asn Pro Cys Ala Asp Arg
            595                 600                 605

Asn Gly Gly Cys Ser His Leu Cys Phe Phe Thr Pro His Ala Thr Arg
        610                 615                 620

Cys Gly Cys Pro Ile Gly Leu Glu Leu Leu Ser Asp Met Lys Thr Cys
625                 630                 635                 640

Ile Val Pro Glu Ala Phe Leu Val Phe Thr Ser Arg Ala Ala Ile His
                    645                 650                 655

Arg Ile Ser Leu Glu Thr Asn Asn Asn Asp Val Ala Ile Pro Leu Thr
                660                 665                 670

Gly Val Lys Glu Ala Ser Ala Leu Asp Phe Asp Val Ser Asn Asn His
            675                 680                 685

Ile Tyr Trp Thr Asp Val Ser Leu Lys Thr Ile Ser Arg Ala Phe Met
        690                 695                 700

Asn Gly Ser Ser Val Glu His Val Val Glu Phe Gly Leu Asp Tyr Pro
705                 710                 715                 720

Glu Gly Met Ala Val Asp Trp Met Gly Lys Asn Leu Tyr Trp Ala Asp
                    725                 730                 735

Thr Gly Thr Asn Arg Ile Glu Val Ala Arg Leu Asp Gly Gln Phe Arg
```

-continued

```
            740                 745                 750
Gln Val Leu Val Trp Arg Asp Leu Asp Asn Pro Arg Ser Leu Ala Leu
    755                 760                 765
Asp Pro Thr Lys Gly Tyr Ile Tyr Trp Thr Glu Trp Gly Gly Lys Pro
    770                 775                 780
Arg Ile Val Arg Ala Phe Met Asp Gly Thr Asn Cys Met Thr Leu Val
785                 790                 795                 800
Asp Lys Val Gly Arg Ala Asn Asp Leu Thr Ile Asp Tyr Ala Asp Gln
                805                 810                 815
Arg Leu Tyr Trp Thr Asp Leu Asp Thr Asn Met Ile Glu Ser Ser Asn
                820                 825                 830
Met Leu Gly Gln Glu Arg Val Val Ile Ala Asp Asp Leu Pro His Pro
                835                 840                 845
Phe Gly Leu Thr Gln Tyr Ser Asp Tyr Ile Tyr Trp Thr Asp Trp Asn
            850                 855                 860
Leu His Ser Ile Glu Arg Ala Asp Lys Thr Ser Gly Arg Asn Arg Thr
865                 870                 875                 880
Leu Ile Gln Gly His Leu Asp Phe Val Met Asp Ile Leu Val Phe His
                885                 890                 895
Ser Ser Arg Gln Asp Gly Leu Asn Asp Cys Met His Asn Asn Gly Gln
                900                 905                 910
Cys Gly Gln Leu Cys Leu Ala Ile Pro Gly Gly His Arg Cys Gly Cys
                915                 920                 925
Ala Ser His Tyr Thr Leu Asp Pro Ser Ser Arg Asn Cys Ser Pro Pro
                930                 935                 940
Thr Thr Phe Leu Leu Phe Ser Gln Lys Ser Ala Ile Ser Arg Met Ile
945                 950                 955                 960
Pro Asp Asp Gln His Ser Pro Asp Leu Ile Leu Pro Leu His Gly Leu
                965                 970                 975
Arg Asn Val Lys Ala Ile Asp Tyr Asp Pro Leu Asp Lys Phe Ile Tyr
                980                 985                 990
Trp Val Asp Gly Arg Gln Asn Ile Lys Arg Ala Lys Asp Asp Gly Thr
                995                 1000                1005
Gln Pro Phe Val Leu Thr Ser Leu Ser Gln Gly Gln Asn Pro Asp
        1010                1015                1020
Arg Gln Pro His Asp Leu Ser Ile Asp Ile Tyr Ser Arg Thr Leu
        1025                1030                1035
Phe Trp Thr Cys Glu Ala Thr Asn Thr Ile Asn Val His Arg Leu
        1040                1045                1050
Ser Gly Glu Ala Met Gly Val Val Leu Arg Gly Asp Arg Asp Lys
        1055                1060                1065
Pro Arg Ala Ile Val Val Asn Ala Glu Arg Gly Tyr Leu Tyr Phe
        1070                1075                1080
Thr Asn Met Gln Asp Arg Ala Ala Lys Ile Glu Arg Ala Ala Leu
        1085                1090                1095
Asp Gly Thr Glu Arg Glu Val Leu Phe Thr Thr Gly Leu Ile Arg
        1100                1105                1110
Pro Val Ala Leu Val Val Asp Asn Thr Leu Gly Lys Leu Phe Trp
        1115                1120                1125
Val Asp Ala Asp Leu Lys Arg Ile Glu Ser Cys Asp Leu Ser Gly
        1130                1135                1140
Ala Asn Arg Leu Thr Leu Glu Asp Ala Asn Ile Val Gln Pro Leu
        1145                1150                1155
```

-continued

```
Gly Leu Thr Ile Leu Gly Lys His Leu Tyr Trp Ile Asp Arg Gln
    1160                1165                1170

Gln Gln Met Ile Glu Arg Val Glu Lys Thr Thr Gly Asp Lys Arg
    1175                1180                1185

Thr Arg Ile Gln Gly Arg Val Ala His Leu Thr Gly Ile His Ala
    1190                1195                1200

Val Glu Glu Val Ser Leu Glu Glu Phe Ser Ala His Pro Cys Ala
    1205                1210                1215

Arg Asp Asn Gly Gly Cys Ser His Ile Cys Ile Ala Lys Gly Asp
    1220                1225                1230

Gly Thr Pro Arg Cys Ser Cys Pro Val His Leu Val Leu Leu Gln
    1235                1240                1245

Asn Leu Leu Thr Cys Gly Glu Pro Pro Thr Cys Ser Pro Asp Gln
    1250                1255                1260

Phe Ala Cys Ala Thr Gly Glu Ile Asp Cys Ile Pro Gly Ala Trp
    1265                1270                1275

Arg Cys Asp Gly Phe Pro Glu Cys Asp Asp Gln Ser Asp Glu Glu
    1280                1285                1290

Gly Cys Pro Val Cys Ser Ala Ala Gln Phe Pro Cys Ala Arg Gly
    1295                1300                1305

Gln Cys Val Asp Leu Arg Leu Arg Cys Asp Gly Glu Ala Asp Cys
    1310                1315                1320

Gln Asp Arg Ser Asp Glu Val Asp Cys Asp Ala Ile Cys Leu Pro
    1325                1330                1335

Asn Gln Phe Arg Cys Ala Ser Gly Gln Cys Val Leu Ile Lys Gln
    1340                1345                1350

Gln Cys Asp Ser Phe Pro Asp Cys Ile Asp Gly Ser Asp Glu Leu
    1355                1360                1365

Met Cys Glu Ile Thr Lys Pro Pro Ser Asp Asp Ser Pro Ala His
    1370                1375                1380

Ser Ser Ala Ile Gly Pro Val Ile Gly Ile Ile Leu Ser Leu Phe
    1385                1390                1395

Val Met Gly Gly Val Tyr Phe Val Cys Gln Arg Val Val Cys Gln
    1400                1405                1410

Arg Tyr Ala Gly Ala Asn Gly Pro Phe Pro His Glu Tyr Val Ser
    1415                1420                1425

Gly Thr Pro His Val Pro Leu Asn Phe Ile Ala Pro Gly Gly Ser
    1430                1435                1440

Gln His Gly Pro Phe Thr Gly Ile Ala Cys Gly Lys Ser Met Met
    1445                1450                1455

Ser Ser Val Ser Leu Met Gly Gly Arg Gly Gly Val Pro Leu Tyr
    1460                1465                1470

Asp Arg Asn His Val Thr Gly Ala Ser Ser Ser Ser Ser Ser Ser
    1475                1480                1485

Thr Lys Ala Thr Leu Tyr Pro Pro Ile Leu Asn Pro Pro Pro Ser
    1490                1495                1500

Pro Ala Thr Asp Pro Ser Leu Tyr Asn Met Asp Met Phe Tyr Ser
    1505                1510                1515

Ser Asn Ile Pro Ala Thr Ala Arg Pro Tyr Arg Pro Tyr Ile Ile
    1520                1525                1530

Arg Gly Met Ala Pro Pro Thr Thr Pro Cys Ser Thr Asp Val Cys
    1535                1540                1545
```

```
Asp Ser Asp Tyr Ser Ala Ser Arg Trp Lys Ala Ser Lys Tyr Tyr
    1550                1555                1560

Leu Asp Leu Asn Ser Asp Ser Asp Pro Tyr Pro Pro Pro Pro Thr
    1565                1570                1575

Pro His Ser Gln Tyr Leu Ser Ala Glu Asp Ser Cys Pro Pro Ser
    1580                1585                1590

Pro Ala Thr Glu Arg Ser Tyr Phe His Leu Phe Pro Pro Pro Pro
    1595                1600                1605

Ser Pro Cys Thr Asp Ser Ser
    1610                1615

<210> SEQ ID NO 3
<211> LENGTH: 5166
<212> TYPE: DNA
<213> ORGANISM: mus musculus

<400> SEQUENCE: 3
```

| | | | | | |
|---|---|---|---|---|---|
| gcccgaggcg | ggagcaagag | gcgccgggag | ccgcgaggat | ccaccgccgc | cgcgcgcgcc | 60 |
| atggagcccg | agtgagcgcg | cggcgctccc | ggccgccgga | cgacatggaa | acggcgccga | 120 |
| cccgggcccc | tccgccgccg | ccgccgccgc | tgctgctgct | ggtgctgtac | tgcagcttgg | 180 |
| tccccgccgc | ggcctcaccg | ctcctgttgt | ttgccaaccg | ccgggatgtg | cggctagtgg | 240 |
| atgccggcgg | agtgaagctg | gagtccacca | ttgtggccag | tggcctggag | gatgcagctg | 300 |
| ctgtagactt | ccagttctcc | aagggtgctg | tgtactggac | agatgtgagc | gaggaggcca | 360 |
| tcaaacagac | ctacctgaac | cagactggag | ctgctgcaca | gaacattgtc | atctcgggcc | 420 |
| tcgtgtcacc | tgatggcctg | gcctgtgact | gggttggcaa | gagctgtac | tggacggact | 480 |
| ccgagaccaa | ccgcattgag | gttgccaacc | tcaatggac | gtcccgtaag | gttctcttct | 540 |
| ggcaggacct | ggaccagcca | agggccattg | ccctggatcc | tgcacatggg | tacatgtact | 600 |
| ggactgactg | gggggaagca | ccccggatcg | agcgggcagg | gatggatggc | agtacccgga | 660 |
| agatcattgt | agactccgac | atttactggc | caatgggct | gaccatcgac | tggaggaac | 720 |
| agaagctgta | ctgggccgat | gccaagctca | gcttcatcca | ccgtgccaac | ctggacggct | 780 |
| ccttccggca | gaaggtggtg | gagggcagcc | tcactcaccc | ttttgccctg | acactctctg | 840 |
| gggacacact | ctactggaca | gactggcaga | cccgctccat | ccacgcctgc | aacaagtgga | 900 |
| cagggggagca | gaggaaggag | atccttagtg | ctctgtactc | acccatggac | atccaagtgc | 960 |
| tgagccagga | gcggcagcct | cccttccaca | caccatgcga | ggaggacaac | ggtggctgtt | 1020 |
| cccacctgtg | cctgctgtcc | ccgagggagc | ctttctactc | ctgtgcctgc | ccactggtg | 1080 |
| tgcagttgca | ggacaatggc | aagacgtgca | agacaggggc | tgaggaagtg | ctgctgctgg | 1140 |
| ctcggaggac | agacctgagg | aggatctctc | tggacacccc | tgacttcaca | gacatagtgc | 1200 |
| tgcaggtggg | cgacatccgg | catgccattg | ccattgacta | cgatccctg | gagggctacg | 1260 |
| tgtactggac | cgacgatgag | gtgcgggcta | tccgcagggc | gtacctagat | ggctcaggtg | 1320 |
| cgcagacact | tgtgaacact | gagatcaatg | accccgatgg | cattgctgtg | gactgggtcg | 1380 |
| cccggaacct | ctactggaca | gatacaggca | ctgacagaat | tgaggtgact | cgcctcaacg | 1440 |
| gcacctcccg | aaagatcctg | gtatctgagg | acctggacga | accgcgagcc | attgtgttgc | 1500 |
| accctgtgat | gggcctcatg | tactggacag | actgggggga | gaaccccaaa | atcgaatgcg | 1560 |
| ccaacctaga | tgggagagat | cggcatgtcc | tggtgaacac | ctcccttggg | tggcccaatg | 1620 |
| gactggcccc | ggacctgcag | gagggcaagc | tgtactgggg | ggatgccaaa | actgataaaa | 1680 |

```
tcgaggtgat caacatagac gggacaaagc ggaagaccct gcttgaggac aagctcccac    1740
acatttttgg gttcacactg ctgggggact tcatctactg gactgactgg cagagacgca    1800
gtattgaaag ggtccacaag gtcaaggcca gtcgggatgt catcattgat caactccccg    1860
acctgatggg actcaaagcc gtgaatgtgg ccaaggttgt cggaaccaac ccatgtgcgg    1920
atggaaatgg agggtgcagc catctgtgct tcttcacccc acgtgccacc aagtgtggct    1980
gccccattgg cctggagctg ttgagtgaca tgaagacctg cataatccct gaggccttcc    2040
tggtattcac cagcagagcc accatccaca ggatctccct ggagactaac aacaacgatg    2100
tggctatccc actcacgggt gtcaaagagg cctctgcact ggactttgat gtgtccaaca    2160
atcacatcta ctggactgat gtcagcctca agacgatcag ccgagccttc atgaatggga    2220
gctcagtgga gcacgtgatt gagtttggcc tcgactaccc tgaaggaatg gctgtggact    2280
ggatgggcaa gaacctctat tgggcggaca cagggaccaa caggattgag gtggcccggc    2340
tggatgggca gttccggcag gtgcttgtgt ggagagacct tgacaacccc aggtctctgg    2400
ctctggatcc tactaaaggc tacatctact ggactgagtg gggtggcaag ccaaggattg    2460
tgcgggcctt catggatggg accaattgta tgacactggt agacaaggtg ggccgggcca    2520
acgacctcac cattgattat gccgaccagc gactgtactg gactgacctg acaccaaca    2580 tgattgagtc ttccaacatg ctgggtcagg agcgcatggt gatagctgac gatctgccct    2640
acccgtttgg cctgactcaa tatagcgatt acatctactg gactgactgg aacctgcata    2700
gcattgaacg ggcggacaag accagtgggc ggaaccgcac cctcatccag ggtcacctgg    2760
acttcgtcat ggacatcctg gtgttccact cctcccgtca ggatggcctc aacgactgcg    2820
tgcacagcaa tggccagtgt gggcagctgt gcctcgccat ccccggaggc caccgctgtg    2880
gctgtgcttc acactacacg ctggaccca gcagccgcaa ctgcagcccg ccctccacct    2940
tcttgctgtt cagccagaaa tttgccatca gccggatgat ccccgatgac cagctcagcc    3000
cggaccttgt cctacccctt catgggctga ggaacgtcaa agccatcaac tatgacccgc    3060
tggacaagtt catctactgg gtggacgggc gccagaacat caagagggcc aaggacgacg    3120
gtacccagcc ctccatgctg acctctccca gccaaagcct gagcccagac agacagccac    3180
acgacctcag cattgacatc tacagccgga cactgttctg gacctgtgag gccaccaaca    3240
ctatcaatgt ccaccggctg gatggggatg ccatgggagt ggtgcttcga ggggaccgtg    3300
acaagccaag ggccattgct gtcaatgctg agcgagggta catgtacttt accaacatgc    3360
aggaccatgc tgccaagatc gagcgagcct ccctggatgg cacagagcgg gaggtcctct    3420
tcaccacagg cctcatccgt cccgtggccc ttgtggtgga caatgctctg ggcaagctct    3480
tctgggtgga tgccgaccta aagcgaatcg aaagctgtga cctctctggg gccaaccgcc    3540
tgaccctgga agatgccaac atcgtacagc cagtaggtct gacagtgctg ggcaggcacc    3600
tctactggat cgaccgccag cagcagatga tcgagcgcgt ggagaagacc actggggaca    3660
agcggactag ggttcagggc cgtgtcaccc acctgacagg catccatgcc gtggaggaag    3720
tcagcctgga ggagttctca gcccatcctt gtgcccgaga caatggcggc tgctcccaca    3780
tctgtatcgc caagggtgat ggaacaccgc gctgctcgtg ccctgtccac ctggtgctcc    3840
tgcagaacct gctgacttgt ggtgagcctc ctacctgctc ccctgatcag tttgcatgta    3900
ccactggtga gatcgactgc atccccggag cctggcgctg tgacggcttc cctgagtgtg    3960
ctgaccagag tgatgaagaa ggctgcccag tgtgctccgc ctctcagttc ccctgcgctc    4020
gaggccagtg tgtggacctg cggttacgct gcgacggtga ggccgactgc caggatcgct    4080
```

-continued

```
ctgatgaagc taactgcgat gctgtctgtc tgcccaatca gttccggtgc accagcggcc    4140
agtgtgtcct catcaagcaa cagtgtgact ccttccccga ctgtgctgat gggtctgatg    4200
agctcatgtg tgaaatcaac aagccaccct ctgatgacat cccagcccac agcagtgcca    4260 tgggcccgt  cattggtatc atcctctccc tcttcgtcat gggcggggtc tactttgtct    4320
gccagcgtgt gatgtgccag cgctacacag gggccagtgg gcccttccc cacgagtatg     4380 ttggtggagc ccctcatgtg cctctcaact tcatagcccc aggtggctca cagcacggtc    4440
ccttcccagg catcccgtgc agcaagtccg tgatgagctc catgagcctg gtggggggc     4500 gcggcagcgt gcccctctat gaccggaatc acgtcactgg ggcctcatcc agcagctcgt    4560
ccagcacaaa ggccacacta tatccgccga tcctgaaccc accccgtcc ccggccacag     4620 acccctctct ctacaacgtg gacgtgtttt attcttcagg cagcccggcc accgctagac    4680
catacaggcc ctacgtcatt cgaggtatgg caccccaac aacaccgtgc agcacagatg     4740
tgtgtgacag tgactacagc accagtcgct ggaagagcag caaatactac ctggacttga    4800
attcggactc agacccctac ccccccccgc ccacccccca cagccagtac ctatctgcag    4860
aggacagctg cccaccctca ccaggcactg agaggagtta ctgccacctc ttcccgcccc    4920
caccgtcccc ctgcacggac tcgtcctgac ctcggccgtc cacccggccc tgctgcctcc    4980
ctgtaaatat ttttaaatat gaacaaagga aaaatatatt ttatgattta aaaaataaat    5040
ataattggga ttttttaacaa gtgagaaatg tgagcggtga aggggtgggc agggctggga   5100
aaactttgta cagtggagaa aatatttata aacttaattt tttaaaacat aaaaaaaaaa    5160
aaaaaa                                                               5166
```

```
<210> SEQ ID NO 4
<211> LENGTH: 1611
<212> TYPE: PRT
<213> ORGANISM: mus musculus

<400> SEQUENCE: 4

Met Glu Thr Ala Pro Thr Arg Ala Pro Pro Pro Pro Pro Pro Pro Leu
1               5                   10                  15

Leu Leu Leu Val Leu Tyr Cys Ser Leu Val Pro Ala Ala Ala Ser Pro
            20                  25                  30

Leu Leu Leu Phe Ala Asn Arg Arg Asp Val Arg Leu Val Asp Ala Gly
        35                  40                  45

Gly Val Lys Leu Glu Ser Thr Ile Val Ala Ser Gly Leu Glu Asp Ala
    50                  55                  60

Ala Ala Val Asp Phe Gln Phe Ser Lys Gly Ala Val Tyr Trp Thr Asp
65                  70                  75                  80

Val Ser Glu Glu Ala Ile Lys Gln Thr Tyr Leu Asn Gln Thr Gly Ala
                85                  90                  95

Ala Ala Gln Asn Ile Val Ile Ser Gly Leu Val Ser Pro Asp Gly Leu
            100                 105                 110

Ala Cys Asp Trp Val Gly Lys Lys Leu Tyr Trp Thr Asp Ser Glu Thr
        115                 120                 125

Asn Arg Ile Glu Val Ala Asn Leu Asn Gly Thr Ser Arg Lys Val Leu
    130                 135                 140

Phe Trp Gln Asp Leu Asp Gln Pro Arg Ala Ile Ala Leu Asp Pro Ala
145                 150                 155                 160

His Gly Tyr Met Tyr Trp Thr Asp Trp Gly Glu Ala Pro Arg Ile Glu
                165                 170                 175
```

```
Arg Ala Gly Met Asp Gly Ser Thr Arg Lys Ile Ile Val Asp Ser Asp
            180                 185                 190

Ile Tyr Trp Pro Asn Gly Leu Thr Ile Asp Leu Glu Glu Gln Lys Leu
        195                 200                 205

Tyr Trp Ala Asp Ala Lys Leu Ser Phe Ile His Arg Ala Asn Leu Asp
    210                 215                 220

Gly Ser Phe Arg Gln Lys Val Val Glu Gly Ser Leu Thr His Pro Phe
225                 230                 235                 240

Ala Leu Thr Leu Ser Gly Asp Thr Leu Tyr Trp Thr Asp Trp Gln Thr
                245                 250                 255

Arg Ser Ile His Ala Cys Asn Lys Trp Thr Gly Glu Gln Arg Lys Glu
            260                 265                 270

Ile Leu Ser Ala Leu Tyr Ser Pro Met Asp Ile Gln Val Leu Ser Gln
        275                 280                 285

Glu Arg Gln Pro Pro Phe His Thr Pro Cys Glu Glu Asp Asn Gly Gly
    290                 295                 300

Cys Ser His Leu Cys Leu Leu Ser Pro Arg Glu Pro Phe Tyr Ser Cys
305                 310                 315                 320

Ala Cys Pro Thr Gly Val Gln Leu Gln Asp Asn Gly Lys Thr Cys Lys
                325                 330                 335

Thr Gly Ala Glu Glu Val Leu Leu Leu Ala Arg Arg Thr Asp Leu Arg
            340                 345                 350

Arg Ile Ser Leu Asp Thr Pro Asp Phe Thr Asp Ile Val Leu Gln Val
        355                 360                 365

Gly Asp Ile Arg His Ala Ile Ala Ile Asp Tyr Asp Pro Leu Glu Gly
    370                 375                 380

Tyr Val Tyr Trp Thr Asp Asp Glu Val Arg Ala Ile Arg Arg Ala Tyr
385                 390                 395                 400

Leu Asp Gly Ser Gly Ala Gln Thr Leu Val Asn Thr Glu Ile Asn Asp
                405                 410                 415

Pro Asp Gly Ile Ala Val Asp Trp Val Ala Arg Asn Leu Tyr Trp Thr
            420                 425                 430

Asp Thr Gly Thr Asp Arg Ile Glu Val Thr Arg Leu Asn Gly Thr Ser
        435                 440                 445

Arg Lys Ile Leu Val Ser Glu Asp Leu Asp Glu Pro Arg Ala Ile Val
    450                 455                 460

Leu His Pro Val Met Gly Leu Met Tyr Trp Thr Asp Trp Gly Glu Asn
465                 470                 475                 480

Pro Lys Ile Glu Cys Ala Asn Leu Asp Gly Arg Asp Arg His Val Leu
                485                 490                 495

Val Asn Thr Ser Leu Gly Trp Pro Asn Gly Leu Ala Leu Asp Leu Gln
            500                 505                 510

Glu Gly Lys Leu Tyr Trp Gly Asp Ala Lys Thr Asp Lys Ile Glu Val
        515                 520                 525

Ile Asn Ile Asp Gly Thr Lys Arg Lys Thr Leu Leu Glu Asp Lys Leu
    530                 535                 540

Pro His Ile Phe Gly Phe Thr Leu Leu Gly Asp Phe Ile Tyr Trp Thr
545                 550                 555                 560

Asp Trp Gln Arg Arg Ser Ile Glu Arg Val His Lys Val Lys Ala Ser
                565                 570                 575

Arg Asp Val Ile Ile Asp Gln Leu Pro Asp Leu Met Gly Leu Lys Ala
            580                 585                 590
```

```
Val Asn Val Ala Lys Val Val Gly Thr Asn Pro Cys Ala Asp Gly Asn
        595                 600                 605
Gly Gly Cys Ser His Leu Cys Phe Phe Thr Pro Arg Ala Thr Lys Cys
        610                 615                 620
Gly Cys Pro Ile Gly Leu Glu Leu Leu Ser Asp Met Lys Thr Cys Ile
625                 630                 635                 640
Ile Pro Glu Ala Phe Leu Val Phe Thr Ser Arg Ala Thr Ile His Arg
                645                 650                 655
Ile Ser Leu Glu Thr Asn Asn Asn Asp Val Ala Ile Pro Leu Thr Gly
            660                 665                 670
Val Lys Glu Ala Ser Ala Leu Asp Phe Asp Val Ser Asn Asn His Ile
        675                 680                 685
Tyr Trp Thr Asp Val Ser Leu Lys Thr Ile Ser Arg Ala Phe Met Asn
    690                 695                 700
Gly Ser Ser Val Glu His Val Ile Glu Phe Gly Leu Asp Tyr Pro Glu
705                 710                 715                 720
Gly Met Ala Val Asp Trp Met Gly Lys Asn Leu Tyr Trp Ala Asp Thr
                725                 730                 735
Gly Thr Asn Arg Ile Glu Val Ala Arg Leu Asp Gly Gln Phe Arg Gln
            740                 745                 750
Val Leu Val Trp Arg Asp Leu Asp Asn Pro Arg Ser Leu Ala Leu Asp
        755                 760                 765
Pro Thr Lys Gly Tyr Ile Tyr Trp Thr Glu Trp Gly Gly Lys Pro Arg
    770                 775                 780
Ile Val Arg Ala Phe Met Asp Gly Thr Asn Cys Met Thr Leu Val Asp
785                 790                 795                 800
Lys Val Gly Arg Ala Asn Asp Leu Thr Ile Asp Tyr Ala Asp Gln Arg
                805                 810                 815
Leu Tyr Trp Thr Asp Leu Asp Thr Asn Met Ile Glu Ser Ser Asn Met
            820                 825                 830
Leu Gly Gln Glu Arg Met Val Ile Ala Asp Asp Leu Pro Tyr Pro Phe
        835                 840                 845
Gly Leu Thr Tyr Ser Asp Tyr Ile Tyr Trp Thr Asp Trp Asn Leu His
    850                 855                 860
Ser Ile Glu Arg Ala Asp Lys Thr Ser Gly Arg Asn Arg Thr Leu Ile
865                 870                 875                 880
Gln Gly His Leu Asp Phe Val Met Asp Ile Leu Val Phe His Ser Ser
                885                 890                 895
Arg Gln Asp Gly Leu Asn Asp Cys Val His Ser Asn Gly Gln Cys Gly
            900                 905                 910
Gln Leu Cys Leu Ala Ile Pro Gly Gly His Arg Cys Gly Cys Ala Ser
        915                 920                 925
His Tyr Thr Leu Asp Pro Ser Ser Arg Asn Cys Ser Pro Pro Ser Thr
    930                 935                 940
Phe Leu Leu Phe Ser Gln Lys Phe Ala Ile Ser Arg Met Ile Pro Asp
945                 950                 955                 960
Asp Gln Leu Ser Pro Asp Leu Val Leu Pro Leu His Gly Leu Arg Asn
                965                 970                 975
Val Lys Ala Ile Asn Tyr Asp Pro Leu Asp Lys Phe Ile Tyr Trp Val
            980                 985                 990
Asp Gly Arg Gln Asn Ile Lys Arg Ala Lys Asp Asp Gly Thr Gln Pro
        995                 1000                1005
Ser Met  Leu Thr Ser Pro Ser  Gln Ser Leu Ser Pro  Asp Arg Gln
```

-continued

```
              1010                1015                1020

Pro His Asp Leu Ser Ile Asp Ile Tyr Ser Arg Thr Leu Phe Trp
    1025                1030                1035

Thr Cys Glu Ala Thr Asn Thr Ile Asn Val His Arg Leu Asp Gly
    1040                1045                1050

Asp Ala Met Gly Val Val Leu Arg Gly Asp Arg Lys Pro Arg Ala
    1055                1060                1065

Ile Ala Val Asn Ala Glu Arg Gly Tyr Met Tyr Phe Thr Asn Met
    1070                1075                1080

Gln Asp His Ala Ala Lys Ile Glu Arg Ala Ser Leu Asp Gly Thr
    1085                1090                1095

Glu Arg Glu Val Leu Phe Thr Thr Gly Leu Ile Arg Pro Val Ala
    1100                1105                1110

Leu Val Val Asp Asn Ala Leu Gly Lys Leu Phe Trp Val Asp Ala
    1115                1120                1125

Asp Leu Lys Arg Ile Glu Ser Asp Leu Ser Gly Ala Asn Arg Leu
    1130                1135                1140

Thr Leu Glu Asp Ala Asn Ile Val Gln Pro Val Gly Leu Thr Val
    1145                1150                1155

Leu Gly Arg His Leu Tyr Trp Ile Asp Arg Gln Gln Gln Met Ile
    1160                1165                1170

Glu Arg Val Glu Lys Thr Thr Gly Asp Lys Arg Thr Arg Val Gln
    1175                1180                1185

Gly Arg Val Thr His Leu Thr Gly Ile His Ala Val Glu Glu Val
    1190                1195                1200

Ser Leu Glu Glu Phe Ser Ala His Pro Cys Ala Arg Asp Asn Gly
    1205                1210                1215

Gly Cys Ser His Ile Cys Ile Ala Lys Gly Asp Gly Thr Pro Arg
    1220                1225                1230

Cys Ser Cys Pro Val His Leu Val Leu Leu Gln Asn Leu Leu Thr
    1235                1240                1245

Cys Gly Glu Pro Pro Thr Cys Ser Pro Asp Gln Phe Ala Cys Thr
    1250                1255                1260

Thr Gly Glu Ile Asp Cys Ile Pro Gly Ala Trp Arg Cys Asp Gly
    1265                1270                1275

Phe Pro Glu Cys Ala Asp Gln Ser Asp Glu Glu Gly Cys Pro Val
    1280                1285                1290

Cys Ser Ala Ser Gln Phe Pro Cys Ala Arg Gly Gln Cys Val Asp
    1295                1300                1305

Leu Arg Leu Arg Cys Asp Gly Glu Ala Asp Cys Gln Asp Arg Ser
    1310                1315                1320

Asp Glu Ala Asn Cys Asp Ala Val Cys Leu Pro Asn Gln Phe Arg
    1325                1330                1335

Cys Thr Ser Gly Gln Cys Val Leu Ile Lys Gln Gln Cys Asp Ser
    1340                1345                1350

Phe Pro Asp Cys Ala Asp Gly Ser Asp Glu Leu Met Cys Glu Ile
    1355                1360                1365

Asn Lys Pro Pro Ser Asp Asp Ile Pro Ala His Ser Ser Ala Ile
    1370                1375                1380

Gly Pro Val Ile Gly Ile Ile Leu Ser Leu Phe Val Met Gly Gly
    1385                1390                1395

Val Tyr Phe Val Cys Gln Arg Val Met Cys Gln Arg Tyr Thr Gly
    1400                1405                1410
```

```
Ala Ser Gly Pro Phe Pro His Glu Tyr Val Gly Gly Ala Pro His
    1415            1420                1425

Val Pro Leu Asn Phe Ile Ala Pro Gly Gly Ser Gln His Gly Pro
    1430            1435                1440

Phe Pro Gly Ile Pro Cys Ser Lys Ser Val Met Ser Ser Met Ser
    1445            1450                1455

Leu Val Gly Gly Arg Gly Ser Val Pro Leu Tyr Asp Arg Asn His
    1460            1465                1470

Val Thr Gly Ala Ser Ser Ser Ser Ser Ser Thr Lys Ala Thr
    1475            1480                1485

Leu Tyr Pro Pro Ile Leu Asn Pro Pro Pro Ser Pro Ala Thr Asp
    1490            1495                1500

Pro Ser Leu Tyr Asn Val Asp Val Phe Tyr Ser Ser Gly Ser Pro
    1505            1510                1515

Ala Thr Ala Arg Pro Tyr Arg Pro Tyr Val Ile Arg Gly Met Ala
    1520            1525                1530

Pro Pro Thr Thr Pro Cys Ser Thr Asp Val Cys Asp Ser Asp Tyr
    1535            1540                1545

Ser Thr Ser Arg Trp Lys Ser Ser Lys Tyr Tyr Leu Asp Leu Asn
    1550            1555                1560

Ser Asp Ser Asp Pro Tyr Pro Pro Pro Pro Thr Pro His Ser Gln
    1565            1570                1575

Tyr Leu Ser Ala Glu Asp Ser Cys Pro Pro Ser Pro Gly Thr Glu
    1580            1585                1590

Arg Ser Tyr Cys His Leu Phe Pro Pro Pro Ser Pro Cys Thr
    1595            1600                1605

Asp Ser Ser
    1610
```

MAMMARY STEM CELL MARKER

CROSS-REFERENCE TO RELATED APPLICATION

This application claims the benefit of U.S. Patent Application No. 60/809,281, filed on May 30, 2006, which is herein incorporated by reference in its entirety.

STATEMENT REGARDING FEDERALLY SPONSORED RESEARCH OR DEVELOPMENT

This invention was made with United States government support awarded by the following agency: NIH RO1 CA113869-01. The United States has certain rights in this invention.

BACKGROUND OF THE INVENTION

The mammary gland is a compound tubulo-alveolar gland that is composed of a series of branched ducts that, during lactation, drain sac-like alveoli (lobules). In the rodents, the mammary epithelium is embedded within a mammary fat pad, whereas in humans, it is embedded within a fibrous and fatty connective tissue. The mammary epithelium is composed of two lineages of epithelial cells: the luminal cells (which make milk during lactation) and basal positioned myoepithelial cells. Like other epithelia, the mammary gland is organized into undifferentiated stem cells and the majority, differentiated cells. Currently, there is no single cell surface biomarker available that allows substantial enrichment of somatic mammary stem cells. All known enrichment protocols rely on combinations of cell surface markers.

While the somatic mammary stem cells (and possibly some of their more immediate descendants that have decreased stem cell potential but still have proliferative potential) may be the targets for malignant transformation, mammary malignancies themselves have been shown to have a cancer stem cell component that propagates the tumor (Al-Hajj M et al. Proc Natl Acad Sci USA 2003,100:3983-8). The presence of tumor stem cells provides an explanation as to why some treatments seem to be effective initially but tumors recur later. Treatments that attack the differentiated tumor cells may not affect the small population of tumor stem cells that actually give rise to tumors. Thus, it is important that the tumor stem cell population be targeted in order for tumors to be successfully contained or eradicated. Cell surface markers for mammary tumor stem cells are of great value in this regard.

Wnt proteins are a family of highly conserved secreted growth factors. Wnt proteins are divided into two types: canonical and noncanonical, and activate different downstream signal transduction pathways. Wnt proteins that are classified as canonical include, but are not limited to Wnt1, Wnt2, Wnt3, Wnt3a, and Wnt8 (Liu G et al. Mol Cell Biol 2005, 25:3475-3482). In the canonical pathway, a Wnt protein initiates signals by binding to a protein complex containing a member of the Frizzled family of seven-transmembrane-domain receptors and a molecule with homology to the low density lipoprotein (LDL) receptor (LRP5 and LRP6) (Logan C Y and R Nusse, Ann Rev Cell Dev Biol 2004, 20:781-810). This down regulates glycogen synthase kinase-3 (GSK3) activity. Normally, GSK3 phosphorylates β-catenin, marking it for ubiquitin-dependent degradation. Thus, GSK3 inhibition results in increased β-catenin levels in the cytosol and nucleus, allowing physical interaction of the Tcf/Lef class of DNA-binding proteins and activation of target promoters (Logan C Y and R Nusse, Ann Rev Cell Dev Biol 2004, 20:781-810).

In addition, other proteins regulate the activity of the Wnt pathway at several levels. Secreted Frizzled-related proteins, Norrin, Dickkopf (DKK), Wise, connective tissue growth factor, and Kremen regulate signaling at the level of the Wnt/Frizzled/LRP interaction while other proteins, including APC, control the pathway intracellularly (Finch P W et al., Proc Natl Acad Sci USA 1997, 94:6770-6775; Wang S M et al. 1997, Biochem Biophys Res Commun 1997, 236:502-504; Xu Q et al. Cell 2004, 116:883-895; Semenov M V et al. Curr Biol 2001, 11:951-961; Mao B et al. Nature 2001, 411: 321-325; Itasaki N et al. Development 2003, 130:4295-4305; Mercurio S et al. Development 2004, 131-2137-2147; and Mao B et al. Nature 2002, 417:664-667). The Dickkopf (DKK) family of secreted proteins are antagonists of the canonical Wnt pathway (Bafico A et al. Nat Cell Biol 2001, 3:683-686; Mao B et al. Nature 2001, 411:321-325). Whereas Wnt-Frizzled interactions may also be involved in non-canonical Wnt signaling events, the LRP5/6 moiety appears to be specifically required for the canonical pathway (Liu G et al. Mol Cell Biol 2005, 25:3475-3482).

Published studies suggest that canonical Wnt signaling plays a significant role during normal mammary gland development (Andl T et al. Dev Cell 2002, 2:643-653; Brisken C et al. Genes Dev 2000, 14:650-654; Hsu W et al. J Cell Biol 2001, 155:1055-1064; Tepera S B et al. J Cell Sci 2003, 116:1137-1149; and van Genderen C et al. Genes Dev 1994, 8:2691-2703). The normal mammary gland development in mice begins at approximately embryonic day 10.5 with the formation of two "mammary lines" (Veltmatt J M et al. Differentiation 2003, 71:1-17). In response to signals from the underlying mesenchyme, the mammary lines give rise to five pairs of lens-shaped mammary placodes which subsequently transform into buds of epithelial cells and sink into dermis. Activation of the canonical Wnt pathway along the mammary lines coincides with the initiation of mammary morphogenesis, and subsequently localizes to mammary placodes and buds (Chu E Y et al. Development 2004, 131:4819-4829). Several Wnt ligands and receptor genes, including LRP5, are expressed during embryonic mammary morphogenesis (Chu E Y et al. Development 2004, 131:4819-4829). Embryos expressing the canonical Wnt inhibitor DKK1 display a complete block in the formation of mammary placodes and mice deficient of Lef-1 fail to maintain their mammary buds (Andl T et al. Dev Cell 2002, 2:643-653; and van Genderen C et al. Genes Dev 1994, 8:2691-2703). DKK1 inhibits the Wnt signaling pathway by binding to LRP5 and LRP6 (Bafico A et al. Nat Cell Biol 2001, 3:683-686).

A connection between mammary stem cells and Wnt1- or β-catenin-induced tumorigenesis has been established. Transgenic expression of these genes result in widespread mammary hyperplasia and rapid tumor formation (Imbert A et al. J Cell Biol 2001, 153:555-568; Nusse R and Varmus H E Cell 1982, 31:99-109; and Tsukamoto A S et al. Cell 1988, 55:619-625). The hyperplastic tissue contains an increased ratio of mammary stem cells which are thought to directly give rise to transformed cells (Li Y et al. Proc Natl Acad Sci USA 2003, 100:15853-15858; Liu B et al. Proc Natl Acad Sci USA 2004, 101:4158-4163; and Shackleton M et al. Nature 2006, 439:84-88). Tumors arising from stem cells often show mixed lineage differentiation (Owens D M and Watt F M Nat Rev Cancer 2003, 3:444-451) and tumors induced by Wnt effectors indeed contain cells from both epithelial lineages (Li Y et al. Proc Natl Acad Sci USA 2003, 100:15853-15858; Liu B et al. Proc Natl Acad Sci USA 2004, 101:4158-4163; and Rosner A et al. Am J Path 2002, 161:1087-1097). The large majority of human breast tumors overexpress cytoplasmic and nuclear levels of β-catenin, a hallmark of activation of the canonical Wnt pathway (Lin S Y et al. Proc Natl Acad Sci USA 2000, 97:4262-4266; and Ryo A et al. Nat Cell Biol 2001, 3:793-801). In addition, many human breast tumors up-regulate Pin1, which inhibits β-catenin degradation by preventing its association with APC (Ryo A et al. Nat Cell Biol 2001, 3:793-801; and Wulf G M et al. EMBO J 2001, 20:3459-3472). Another recent report links amplification and overexpression of Dishevelled1, a positively acting component of the pathway upstream of GSK3, to breast cancer (Nagahata T et al. Cancer Sci 2003, 94:515-518). Further, recent reports have linked down-regulation of the secreted Wnt inhibitors sFRP1 and Wif1 to breast cancer (Ugolini F et al. Oncogene 2001, 20:5810-5817; Klopocki E et al. Int J Oncol 2004, 25:641-649; and Wismann C et al. J Pathol 2003, 201:204-212).

BRIEF SUMMARY OF THE INVENTION

It is disclosed here that low density lipoprotein receptor-related protein 5 (LRP5) is a cell surface marker for somatic mammary stem cells and mammary tumor stem cells. The identification of LRP5 as a cell surface marker for the above stem cells provides new tools for enriching these stem cells. Methods of screening for agents that modulate LRP5 activity, of treating mammary tumor or breast cancer, of imaging somatic mammary stem cells and mammary tumor stem cells in vivo, and of assessing prognosis of human breast cancer are also provided.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 3 shows that the absence of Lrp5 delays normal mammary development. A, representative whole mount preparations (stained with carmine to reveal the mammary ductal tree) are shown for juvenile (5-week) and mature (11-week) virgin female mice. The arrows indicate typical terminal end buds. LN, lymph node. The result of morphometric analysis of the average number of TEBs at 5 weeks (B) and branches per gland at 11 weeks (C). In the absence of Lrp5 the number of TEBs is reduced by 42% (p=0.0003, 2-tailed t test assuming unequal variances), and the number of branches per gland is reduced by 46% (p=0.001, 2-tailed t test assuming unequal variances) compared with Lrp5$^{+/+}$ littermate controls.

FIG. 4 shows the results of stem cell activity assays. Mammary epithelial cells were isolated from Lrp5$^{-/-}$ and control mice, and different numbers of cells were transferred to cleared fat pads to test their outgrowth potential. The fraction of cleared fat pads colonized by cells is shown in panel A. Numbers above columns represent the number of glands colonized per total number of glands transplanted. The morphogenesis of a representative outgrowth from 5,000 Lrp5$^{+/+}$ cell inocula and lack of outgrowth from 5,000 Lrp5$^{-/-}$ cell inocula is shown in panel B.

FIG. 6 shows in vivo stem cell activity of FACS sorted LRP5 high (top 5.13%) and negative mammary epithelial cells. Mammary epithelial cells were isolated from 10-week, virgin Balb/c mice and stained for LRP5. LRP5 high (top 5.13%), negative, and total population mammary epithelial cells were FACS sorted (see description for FIG. 5 above). The sorted cells were then transplanted into cleared fat pads of 3-week Balb/c recipient mice. Following 8 weeks, mammary glands were harvested, carmine stained, and scored for primary outgrowths.

FIG. 8 shows normalized Lrp5 expression levels (mRNA) in 275 breast cancer patients grouped into the following two classes: class 1 (196 patients)-breast cancer patients who are cancer-free at the 5 year time point from first diagnosis; and class 2 (79 patients)—breast cancer patients who still have cancer (either the original cancer or recurrence) or have died at the 5 year time point from first diagnosis. The line near the middle of the box for each class is the median normalized expression value of Lrp5. Each box captures 25th percentile to 75th percentile of the patients in terms of normalized Lrp5 expression level. The top and bottom bars indicate the 100 percentile and 0 percentile, respectively. The dot above and below the box indicate outliers. The scale is a log2 scale which means that from 0 to 1 there is a 2-fold increase in expression, 0 to 2 4-fold increase, 0 to 3 8-fold increase, and 0 to 4 16-fold increase. T-test was performed to analyze the difference in Lrp5 expression between the two classes of patients and we obtained a P value of $8.8 \times 10^{-5}$.

FIG. 9 shows normalized Lrp5 expression levels (mRNA) in 295 breast cancer patients grouped into the following two classes: class 1 (194 patients)—breast cancer patients who are metastasis-free from first diagnosis for 5 years; and class 2 (101 patients)—breast cancer patients with metastasized cancer (within 5 years of first diagnosis). The line near the middle of the box for each class is the median normalized expression value of Lrp5. Each box captures 25th percentile to 75th percentile of the patients in terms of normalized Lrp5 expression level. The top and bottom bars indicate the 100 percentile and 0 percentile, respectively. The dot above and below the box indicate outliers. The scale is a log2 scale which means that from 0 to 1 there is a 2-fold increase in expression; 0 to 2, a 4-fold increase; 0 to 3, an 8-fold increase; and 0 to 4, a 16-fold increase. A t-test was performed to analyze the difference in Lrp5 expression between the two classes of patients and we obtained a P value of $3.5 \times 10^{-6}$.

DETAILED DESCRIPTION OF THE INVENTION

Figure 1:
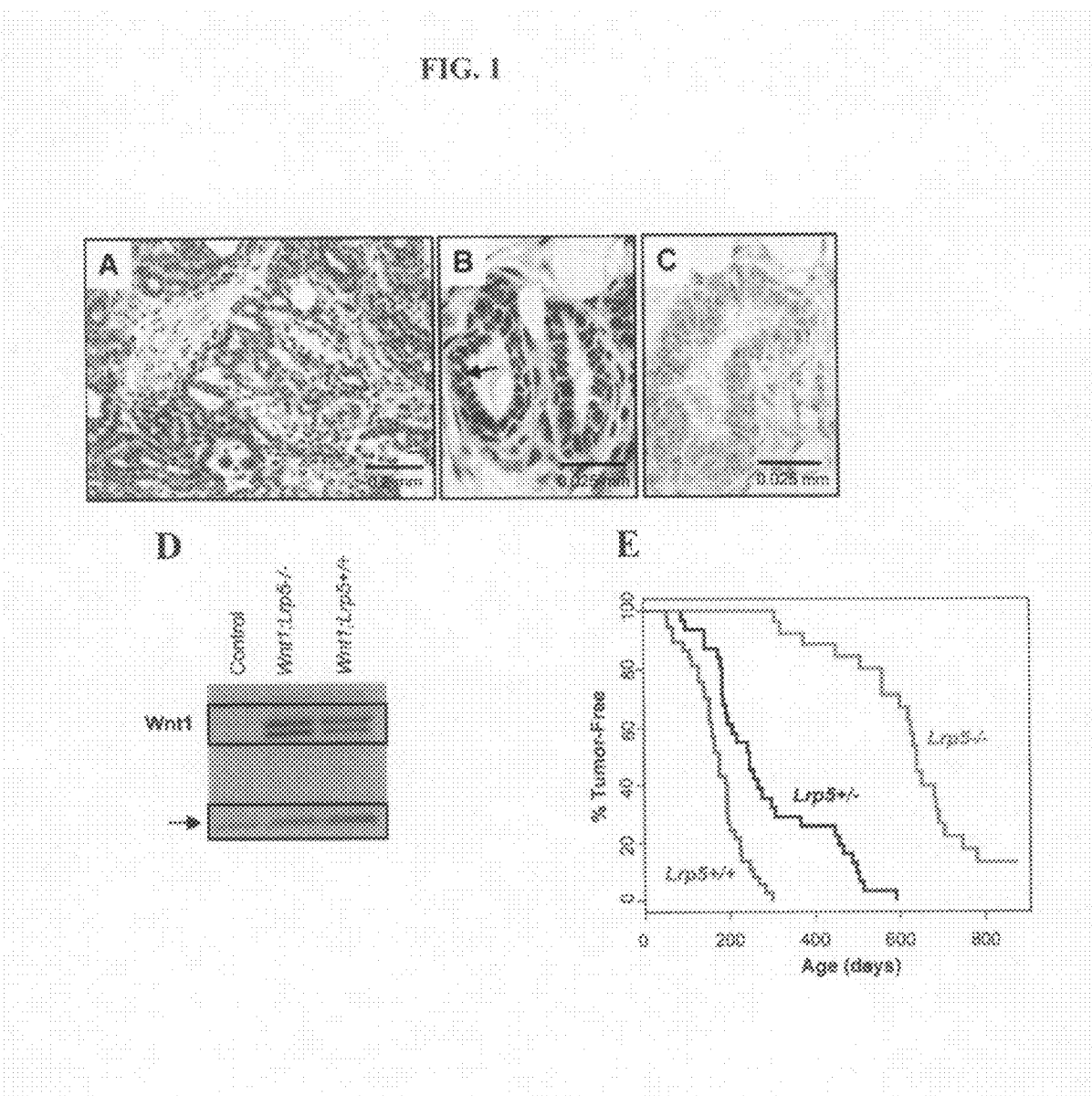
FIGS. 1A-C show immunohistochemical stainings using an LRP5-specific polyclonal antibody. LRP5 is expressed in Wnt1-induced tumors (A) and in a fraction of mammary ductal cells from hyperplastic Wnt1 transgenic mammary gland (B). The arrow indicates a representative cell with positive staining. No staining was observed in Wnt1;Lrp5$^{-/-}$ mammary ductal cells (C).
FIG. 1D shows Western blot of total protein from MMTV-Wnt1 transgenic Lrp5$^{+/+}$ or Lrp5$^{-/-}$ mammary glands, which indicates that the expression of the Wnt1 transgene is not affected by the Lrp5 genotype. Protein from a normal mammary gland was used as a negative control (left lane). The arrow indicates a nonspecific band to monitor equal loading.
FIG. 1E shows that the emergence of Wnt1-induced mammary tumors is delayed in Lrp5$^{-/-}$ mice. Thirty-seven Lrp5$^{+/+}$, 31 Lrp5$^{+/-}$, and 26 Lrp5$^{-/-}$ Wnt1 transgenic female mice were palpated weekly and dates of tumor appearance recorded. Data are plotted as the proportion of mice in each of the three genotypes remaining tumor free as a function of days of age.

It is disclosed here that Wnt signaling receptor LRP5 is, highly expressed in a fraction of mammary epithelial cells that contains somatic mammary stem cell activity. The inventors established co-localization of mammary epithelial cells having high LRP5 expression with the somatic mammary stem cell-enriched fraction and determined the enhanced stem cell function of the LRP5 high fraction. In situ examination of LRP5 expression confirmed the heterogeneous expression of LRP5 and located the LRP5 high cells in the mammary ductal cell population. The inventors also generated LRP5 null (knockout) mice and observed that although mammary glands developed in these mice, the adult mammary epithelial cell populations had negligible stem cell activity. LRP5 null mice were also found to be resistant to Wnt1-induced mammary tumors. Similar to somatic mammary stem cells, it is expected that mammary tumor stem cells also express high levels of LRP5, and require this signaling receptor for survival. Although the observations disclosed here were made with mice, it is expected that they also apply to other mammals such as humans and rats given that the Wnt pathway, and mammary gland development, are highly conserved across the mammalian species.

The disclosure here provides new tools for enriching somatic mammary stem cells and mammary tumor stem cells. Methods of screening for agents that may modulate LRP5 activity, of treating mammary tumor or breast cancer, and of monitoring somatic mammary stem cells and mammary tumor stem cells in vivo are also provided. In some embodiments, the methods of the present invention are practiced with human, mouse, or rat mammary cells or human, mouse, or rat mammary tumor cells.

It is further disclosed here that human breast cancer patients with poor prognosis express a higher level of LRP5 in the mammary tumor cells (on average) than those with good prognosis. As shown in Example 4 below, the population of breast cancer patients who still have cancer (either the original cancer or recurrence) or have died at the 5 year time point from first diagnosis expresses a higher level of LRP5 in the tumor cells (the median level of expression) than the population of breast cancer patients who are cancer-free at the 5 year time point from first diagnosis. Further, the population of breast cancer patients with metastasis (within 5 years of initial diagnosis) expresses a higher level of LRP5 in the tumor cells (the median level of expression) than the population of breast cancer patients who are metastasis-free (within 5 years of initial diagnosis). Therefore, LRP5 can serve as a prognostic marker for breast cancer.

The term "somatic mammary stem cells" used herein refers to the cells that can generate both the ductal and lobular structures of the mammary gland, can generate all the cell lineages of the mammary epithelium (e.g., luminal cells and myoepithelial cells), and can self-renew. For example, when transplanted to a mammary fat pad in a mouse or rat in vivo, a somatic mammary stem cell can generate a functional ductal tree. Somatic mammary stem cells can also generate mammary progenitor cells. The progenitor cells have proliferative capability and are the immediate precursors to the differentiated mammary cells such as luminal cells and myoepithelial cells. Mammary progenitor cells can be detected by their ability to generate colonies in vitro.

The term "mammary tumor stem cells" is used herein to refer to mammary tumor cells that are tumorigenic, i.e., that they can give rise to tumorigenic cells (self-renew) and non-tumorigenic tumor cells ("differentiation"). For example, a mammary tumor stem cell can form a new tumor when grafted to a mammary fat pad of a mouse (e.g., a nude mouse, a NOD immuno-deficient mouse, or a NOD/SCID immuno-deficient mouse). Mammary tumor stem cells can be analyzed using dilution xenograft assays.

As used herein, "antibody" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). For example, the term includes bivalent or bispecific molecules, diabodies, triabodies, and tetrabodies. Bivalent and bispecific molecules are described in, e.g., Kostelny et al. J Immunol 1992, 148:1547, Pack and Pluckthun Biochemistry 1992, 31:1579, Zhu et al. Protein Sci 1997, 6:781, Hu et al. Cancer Res. 1996, 56:3055, Adams et al. Cancer Res. 1993, 53:4026, and McCartney, et al. Protein Eng. 1995, 8:301. The term "antibody" also includes antigen binding forms of antibodies, including fragments with antigen-binding capability (e.g., Fab', F(ab')$_2$, Fab, Fv and rIgG). The term also refers to recombinant single chain Fv fragments (scFv). Preferably, antibodies employed to practice the present invention bind to a selected target antigen on the surface of a cell with an affinity (association constant) of greater than or equal to $10^7$ $M^{-1}$.

When an antibody is referred to as specific for a particular antigen, it means that the binding reaction is determinative of the presence of the antigen in a heterogeneous population of proteins and other biologics. Thus, under suitable conditions, the specified antibodies bind to a particular protein sequences at least two times the background and more typically more than 10 to 100 times the background.

In one aspect, the present invention relates to a method for enriching somatic mammary stem cells from a population of mammary cells. The method includes the steps of obtaining a population of mammary cells containing one or more somatic mammary stem cells (e.g., a mammary cell population that includes the total mammary epithelial cell population or a substantial portion thereof that is essentially free of adipocyte contamination), contacting said population of mammary cells with an anti-LRP5 antibody, and selecting cells that bind to the antibody. Preferably, at least 1%, 2%, 3%, 4%, 5%, 6%, or 7% of the selected cells are somatic mammary stem cells. As Shackleton M et al. (Nature 439:84-88, 2006) estimated that mammary stem cells occur at a frequency of about 1 in 1,300 total mammary cells in mice, a 1% mammary stem cell concentration represents a 13-fold enrichment. While other methods of enriching for mammary stem cells that involve the use of cell surface markers are known, these methods require a combination of at least two cell surface markers (see e.g., "Stingl J et al. Nature 2006, 439:993-997" for the use of cell surface markers CD49f and CD24). The method provided here uses a single marker (LRP5) and can achieve a comparable enrichment level to the methods that involve the use of multiple markers.

It is well within the capability of a skilled artisan to isolate mammary cells from a mammary gland. One example is provided in example 2 below (see also Stingl J et al. Nature 2006, 439:993-997, which is herein incorporated by reference in its entirety). Other methods are known in the art. Typically, known procedures provide a population of mammary cells that is essentially free of adipocyte contamination but includes mammary epithelial cells, stromal cells (e.g., fibroblasts and other connective tissue cells), endothelial cells, and hematopoietic cells. Methods of isolating mammary epithelial cells are also well known in the art (see e.g., Gould MN et al. Cancer Res 1986, 46:4942-4945, which is herein incorporated by reference in its entirety). Somatic mammary stem cells can be enriched using the LRP5 marker for positive selection from the population of mammary cells. Optionally, a somatic mammary stem cell "negative marker" (i.e., a marker not present on the cell surface of somatic mammary stem cells) is used for negative selection (i.e., for the elimination of cells that are not somatic mammary stem cells). For example, endothelial cell markers CD31 and Von Willebrand factor, hematopoietic cell markers CD45 and Ter119, and stromal cell marker CD140a can be used to eliminate certain endothelial, hematopoietic, and stromal cells to facilitate the enrichment of somatic mammary stem cells. Depending on the particular enrichment techniques, the negative markers can be used to eliminate certain non-mammary stem cells before the positive selection with LRP5 or the positive and negative selections can be accomplished in one step. As an example for the former, antibodies to one or more of CD31, Von Willebrand factor, CD45, Ter119, and CD140a can be conjugated to a matrix such as magnetic beads to deplete the non-epithelial cells. The leftover epithelial enriched population of mammary cells is then labeled with fluorochrome-conjugated LRP5 antibodies for enriching somatic mammary stem cells by, for example, flow cytometry. As an example for the latter, antibodies to one or more of CD31, CD45, Ter119, and CD140a and antibodies to LRP5 can be conjugated to different fluorochrome so that endothelial, stromal, and/or hematopoietic cells can be gated out from LRP5 flow cytometry enrichment. Similarly, one or more mammary epithelial cell surface markers can optionally be used to enrich for mammary epithelial cells first before the LRP5 marker is used to enrich for somatic mammary stem cells.

Any agent that can bind to the cell surface markers can be used to practice the present invention. Antibodies specific for the markers are examples of such agents.

cDNA and amino acid sequences for LRP5 in various species are available and it is well within the capability of a skilled artisan to generate specific antibodies to these proteins if they are not already available. The human LRP5 cDNA and amino acid sequences are provided in the sequence listing at SEQ ID NO: 1 and 2, respectively. The mouse LRP5 cDNA and amino acid sequences are provided in the sequence listing at SEQ ID NO:3 and 4, respectively. The rat LRP5 cDNA and amino acid sequences can be found at GenBank Accession numbers XM_215187.4 and XP_215187.3, respectively. The chimpanzee LRP5 cDNA and amino acid sequences can be found at GenBank Accession number XM_508605.2. The monkey LRP5 cDNA and amino acid sequences can be found at GenBank Accession number XP_001115564.1. The cow LRP5 cDNA and amino acid sequences can be found at GenBank Accession number XM_614220.3. The rabbit LRP5 cDNA and amino acid sequences can be found at GenBank Accession numbers AB017499.1 and BAA33052.1, respectively.

In some embodiments, flow cytometry is employed to conduct the positive selection and, if applicable, the negative selection as well. A skilled artisan is familiar with flow cytometry-related techniques such as labeling targeted cells (e.g., somatic mammary stem cells) with cell surface marker antibodies (e.g., anti-LRP5 antibodies), setting suitable parameters for sorting and collecting labeled cells, and collecting the targeted cells (see e.g., Givan A, Flow Cytometry: First Principles, Wiley-Liss, New York, 1992; and Owens M A & Loken M R, Flow Cytometry: Principles for Clinical Laboratory Practice, Wiley-Liss, New York, 1995). As shown in Example 2 below, flow cytometry analysis of mammary epithelial cells stained for LRP5 revealed a gradient of LRP5 expression from negative to high levels. For the purpose of the present invention, a population of LRP5 high mammary epithelial cells is taken for the enrichment of somatic mammary stem cells. By LRP5 high mammary epithelial cells, we mean the top 10% of the total mammary epithelial cell population in terms of LRP5 expression level at the cellular surface. For example, a population of mammary epithelial cells defined by any percentage ranging from the top 10% to the top 1% of total mammary epithelial cell population in terms of LRP5 expression level at the cellular surface can be taken for the enrichment of somatic mammary stem cells. In certain embodiments, a population of mammary epithelial cells defined by a percentage ranging from the top 9% to the top 1%, from the top 8% to the top 1%, from the top 7% to the top 1%, from the top 6% to the top 1%, from the top 5% to the top 1%, from the top 4% to the top 1%, from the top 3% to the top 1%, or from the top 2% to the top 1% of total mammary epithelial cell population in terms of LRP5 expression level at the cellular surface is taken for the enrichment of somatic mammary stem cells. Said enrichment for somatic mammary stem cells can be achieved by collecting the top 10 or smaller percentage (e.g., any percentage ranging from the top 10% to the top 1%) of a mammary cell population (in terms of LRP5 expression level at the cellular surface) that includes the total mammary epithelial cell population or a substantial portion thereof and is essentially free of adipocyte contamination. In one form, the mammary cell population has been depleted of certain endothelial cells, hematopoietic cells, and/or stroma cells using one or more of the following markers: CD31, Von Willebrand factor, CD45, Ter119, and CD140a. For example, the mammary cell population can be depleted of CD31+ cells. By a substantial portion of the total mammary epithelial cell population, we mean at least 70%, 80%, 90%, or 95% of the total mammary epithelial cell population.

In some embodiments, a matrix such as magnetic beads to which an antibody (e.g., an anti-LRP5 antibody) can be conjugated directly or indirectly is employed to conduct the positive selection and, if applicable, the negative selection as well. In this regard, targeted cells can be separated from other cells by binding to the matrix through the antibody. When the matrix is used for positive selection in connection with an anti-LRP5 antibody, a skilled artisan can readily adjust and find suitable binding conditions so that LRP5 high mammary epithelial cells are bound to the matrix while other mammary epithelial cells (LRP5 negative and LRP5 low) are not.

In some other embodiments, flow cytometry is used to conduct the positive selection and a matrix described above is used to conduct the negative selection or vise versa.

Antibodies (e.g., anti-LRP5 antibodies) useful in the present invention can be labeled with a marker or they may be conjugated to a matrix. In some embodiments, the marker is used to conjugate the antibodies to the matrix. Examples of markers include biotin, which can be removed by avidin bound to a support, and fluorochromes (e.g. fluorescein), which provide for separation using fluorescence activated sorters. Examples of matrices include magnetic beads, which allow for direct magnetic separation (Kemshead J T, J Hematother 1992;1:35-44), panning surfaces such as plates, (Lebkowski J S et al., J. of Cellular Biochemistry supple. 1994, 18b:58), dense particles for density centrifugation (Van Vlasselaer P, Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), dense particles alone (Zwerner et al., Immunol. Meth. 1996, 198:199-202), adsorption columns (Berenson et al., Journal of Immunological Methods 1986, 91:11-19), and adsorption membranes.

The antibodies may be directly or indirectly coupled to a matrix. For example, the antibodies may be chemically bound to the surface of magnetic particles (e.g., using cyanogen bromide). When the magnetic particles are reacted with a sample, conjugates will form between the magnetic particles with bound antibodies and the cells having the corresponding markers on their surfaces. Alternatively, the antibodies may be indirectly conjugated to a matrix. For example, the antibodies may be biotinylated and indirectly conjugated to a matrix which is labeled with avidin. Magnetic iron-dextran particles that are covalently labeled with avidin (Miltenyi S et al., Cytometry 1990, 11:231) can be used in this regard. Many alternative indirect ways to specifically cross-link the antibodies and matrices would also be apparent to those skilled in the art.

As another example, a matrix may be coated with a second antibody having specificity for the antibodies against the cell surface markers. By way of example, if the antibodies against the cell surface markers are mouse IgG antibodies, the second antibody may be rabbit anti-mouse IgG.

As another example, bispecific antibodies and tetrameric antibody complexes can be used. Bispecific antibodies contain a variable region of an antibody specific for a cell surface marker and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (Proc Natl Acad Sci USA 1986, 83:1453) and Staerz & Bevan, (Immunology Today 1986, 7:241). Bispecific antibodies may also be constructed by chemical means using procedures such as those described by Staerz et al. (Nature 1985, 314:628) and Perez et al. (Nature 1985, 316:354), or by expression of recombinant immunoglobulin gene constructs.

A tetrameric immunological complex may be prepared by mixing a first monoclonal antibody which is capable of binding to an antigen on the surface of a matrix and a second monoclonal antibody specific for a cell surface marker. The first and second monoclonal antibodies are from a first animal species. The first and second antibody are reacted with an about equimolar amount of monoclonal antibodies of a second animal species which are directed against the Fc-fragments of the antibodies of the first animal species. The first and second antibodies may also be reacted with an about equimolar amount of the $F(ab')_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles having a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. in J. Hematotherapy 1992, 1:35-44, at pages 36 to 39 and Ziolo et al. Science 1994, 257:219 which are incorporated herein by reference. Colloidal particles of dextran-iron complex are preferably used in the process of the invention (Molday, R. S. and McKenzie, L. L. FEBS Lett. 1984, 170:232; Miltenyi et al. Cytometry 1990, 11:231; Molday, R. S. and MacKenzie, D., J. Immunol. Methods 1982, 52:353; Thomas et al., J. Hematother. 1993, 2:297; and U.S. Pat. No. 4,452,733, which are each incorporated herein by reference).

In accordance with the magnetic separation method, a sample containing the cells to be recovered, is reacted with an antibody specific for a cellular surface marker of the cells so that the antibody binds to the cells present in the sample to form cell conjugates of the targeted cells and the antibody. The reaction conditions are selected to provide the desired level of binding of the targeted cells and the antibody. The concentration of the antibody is selected depending on the estimated concentration of the targeted cells in the sample. The magnetic particles are then added and the mixture is incubated for a suitable period of time at a suitable temperature. The sample is then ready to be separated in a magnetic device.

In another aspect, the present invention relates to a method of enriching mammary tumor stem cells from a population of mammary tumor cells. The method includes the steps of obtaining a population of mammary tumor cells containing one or more mammary tumor stem cells, contacting said population of mammary tumor cells with an anti-LRP5 antibody, and selecting cells that bind to the antibody. Preferably, at least 1%, 2%, 3%, 4%, 5%, 6%, or 7% of the selected cells are mammary tumor stem cells. Also preferably, the mammary tumor stem cells are enriched for at least 2-fold, 3-fold, 5-fold, 7-fold, or 10-fold relative to the original tumor from which said population is derived (unfractionated tumor cells). Reagents and procedures for enriching somatic mammary stem cells can be used similarly here for enriching mammary tumor stem cells.

In another aspect, the present invention relates to a method for forming a mammary tumor in an animal such as a mammal (e.g., a mouse or rat). The method includes the step of introducing a population of mammary tumor cells enriched for mammary tumor stem cells into the animal (e.g., a mammary fat pad), wherein said population is derived from a solid mammary tumor and the mammary tumor cells in said population express LRP5.

In another aspect, the present invention relates to a method for screening for an agent that may modulate (either inhibit or enhance) LRP5 activity in a cell. The method includes the steps of providing a cell that has attenuated LRP6 activity (e.g., the LRP6 activity is reduced by at least 80%, 90%, or 95%), exposing the cell to a test agent, determining the LRP5 activity in the cell, and comparing the LRP5 activity to that of a control cell (the same type of cell as the exposed cell) not exposed to the test agent wherein a higher or lower LRP5 activity in the exposed cell than that of the control cell indicates that the agent can modulate LRP5 activity. If the cell does not express any Wnt ligand or produces an insufficient amount of Wnt for the purpose of conducting the screening assay, a Wnt ligand such as Wnt1, Wnt2, Wnt3, Wnt3a, or Wnt8 (e.g., Wnt1 or Wnt3a) may be added exogenously to stimulate Wnt signaling through LRP5. Alternatively, a DNA construct for expressing a Wnt ligand (e.g., a Wnt expression vector) can be introduced into the cell to express a Wnt protein.

A cell with attenuated LRP6 activity can be provided by using a LRP6-specific antibody to block its activity or by using antisense oligonucleotides, siRNA, or shRNA to block LRP6 gene expression so that the level of LRP6 protein in the cell is reduced by at least 80%, 90%, or 95% (see e.g., Young J J et al. PLoS Pathog 2007, 3:e27). Agents that can inhibit LRP5 activity specifically are useful for treating mammary tumor or breast cancer.

Optionally, a cell that has wild-type LRP6 activity can also be employed in the screening assay as a control to select for agents that specifically modulate LRP5-mediated signaling. Those agents that can modulate Wnt signaling in LRP6 attenuated cells but not wild-type LRP6 control cells are identified as specific modulators of LRP5-mediated signaling.

In a preferred embodiment, a LRP6 null (knockout) cell is used in the screening. By a LRP6 null cell, we mean that no detectable level of functional LRP6 is produced. Such a cell can be provided by, for example, introducing one or more mutations into the LRP6 nucleic acid gene sequence (including complete deletion of the gene sequence). In one form, the LRP6 gene is disrupted so that the cell does not express any part of the LRP6 coding sequence at the mRNA level. Preferably, both chromosomal copies of the LRP6 nucleic acid sequence are disrupted in the cell.

A LRP6 null animal such as a LRP6 null mouse or rat can be a source of LRP6 null cells. Null or knockout animals such as knockout mice and rats are routinely generated in the art. For example, LRP6 knockout (LRP6$^{-/-}$) mice have been generated by Pinson K I et al. (Nature 2000, 407:535-538). Given that LRP6 knockout mice die around birth, fetuses (full term or not) can be rescued by caesarean section. A LRP6 knockout rat can be generated by a variety method such as that described in published U.S. patent application 20030150001, which is herein incorporated by reference in its entirety. The term null or knockout animals are used broadly to encompass a knockout fetus and as well as a knockout neonate and adult animal.

The LRP6 gene may be disrupted using a variety of technologies familiar to those skilled in the art. For example, a stop codon may be introduced into the gene by homologous recombination. Alternatively, a deletion may be introduced into the gene by homologous recombination. In some embodiments, stop codons may be introduced into all reading frames in the sequence downstream of the deletion to eliminate artifactual translation products. In further embodiments, the gene may be disrupted by inserting a gene encoding a marker protein, for example, via homologous recombination.

Examples of suitable cells that can be used in the screening method include murine (mouse or rat) embryonic fibroblasts (MEFs), primary keratinocyte cultures (e.g., mouse or rat primary keratinocyte cultures), and murine (mouse or rat) embryonic stem cells. A skilled artisan can readily isolate from Lrp6$^{-/-}$ murine animals murine embryonic fibroblasts from mid-gestational embryos, primary keratinocyte cultures from later stage embryos, or murine embryonic stem cells. For example, to establish murine embryonic fibroblast lines, one can isolate Lrp6$^{-/-}$ embryos (or control littermate embryos) at embryonic day 12 or 13, remove the head and internal organs, and then disassociate the remaining tissue with a razor blade in the presence of trypsin. These cells will be useful for up to 6-7 passages.

LRP5 activity can be measured by any part of the Wnt pathway at or downstream of LRP5. For example, the level of LRP5 at the mRNA or protein level can be measured. Phosphorylation of the C-terminus of LRP5 can also be measured. Alternatively, the activity of glycogen synthase kinase-3 (GSK3) activity can be measured. An increase in GSK3 activity indicates an inhibition of LRP5 activity and a decrease in GSK3 activity indicates an increase in LRP5 activity. β-catenin level such as that in the cytosol and/or nucleus can also be measured as a reflection of LRP5 activity. An increase in β-catenin level indicates an increase in LRP5 activity and vise versa. In one embodiment, the β-catenin level in the nucleus is measured wherein an increase in level indicates more LRP5 activity and vise versa. Alternatively, a Wnt reporter construct containing a reporter operably linked to a suitable promoter responsive to Wnt pathway activity can be provided in a cell for measuring LRP5 activity. Examples of suitable promoters include promoters for Wnt/β-catenin-responsive genes such as Axin2, CyclinD1, PPAR-delta, TCF, and LEF1 (see e.g., Yan D et al. Proc Natl Acad Sci USA 2001, 98:14973-8; Lustig B et al. Mol Cell Biol 2002, 22:1184-93; Jho E H et al. Mol Cell Biol 2002, 2:1172-83; Tetsu 0 et al. Nature 1999, 398:422-6; Shtutman M et al. Proc Natl Acad Sci USA 1999, 96:5522-7; He T C et al. Cell 1999, 99:335-45; Roose J et al. Science 1999, 285:1923-6; Hovanes K et al. Nat Genet 2001, 28:53-7; and Filali M et al. J Biol Chem 2002, 277:33398-410). A skilled artisan is familiar with these promoters. For example, a TCF-luciferase reporter gene assay (TOPFLASH) is commercially available (Mao et al. Nature 2001, 411:321-325).

Additional examples of Wnt/β-catenin-responsive genes include c-myc, c-jun, fra-1, uPAR, matrix metalloproteinase MMP-7, Nr-CAM, ITF-2, Gastrin, CD44, EphB/ephrin-B, BMP4, claudin-1, Survivin, VEGF, FGF18, Hath1, Met, endothelin-1, c-myc binding protein, L1 neural adhesion, Id2, Tiam1, Nitric Oxide, Synthase 2, Dickkopf, FGF9, FGF20, Sox9, Runx2, SALL4, RANK ligand, CCN1/Cyr61, Sox2, Pituitary tumor transforming gene (PTTG), Delta-like 1, FoxN1, matrix metalloproteinase-26, nanog, Frizzled 7, Follistatin, Siamois, fibronectin, myogenic bHLH, engrailed-2, Xnr3, connexin43, twin, connexin 30, retinoic acid receptor gamma, dharma/bozozok, MITF/nacre, Wrch-1, TNF family 41 BB ligand, ephrinB1, Stra6, autotoxin, ISLR, Twist, Stromelysin, WISP, Brachyury, Proglucagon, Osteocalcin, cyclooxygenase-2, Irx3, Six3, neurogenin 1, WISP-1, WISP-2, IGF-II, Proliferin-2, Proliferin-3, Emp, IGF-I, VEGF-C, MDR1, IL-6, periostin, Cdx1, Cdx4, betaTrCP, sFRP-2, Pitx2, EGF receptor, Eda (TNF-related), E-cadherin, Keratin, movol, Jagged1, mBTEB2, FGF4, Interleukin8, ret, connexin43, versican, Ubx, wingless, Dpp, Engrailed, Dfrizzled2, shavenbaby, stripe, and Nemo.

A reporter gene is defined broadly here to refer to a DNA sequence whose expression in a cell can be measured. Preferably, the reporter gene produces a polypeptide product whose function can be measured. Examples of such reporter genes include but are not limited to a β-galactosidase gene, a luciferase gene, and a green fluorescent protein (GFP) gene. An increase in the expression (at the mRNA or protein level) or activity of the reporter gene indicates an increase in LRP5 activity and vise versa. As another example, the reporter gene can be an inhibitor of the expression of a killer gene (the product of which lead to the death of the host cell) from another expression construct introduced into the cell. This is especially useful for screening for agents that can inhibit the activity of LRP5. For example, when an agent sufficiently inhibits the activity of LRP5, the expression of reporter gene will be sufficiently inhibited resulting in the expression of the killer gene and in turn the death of the cell. In this regard, cell death is the end point of the screening.

In another aspect, the present invention relates to a method for inhibiting the proliferation or causing the death of a mammary tumor cell that expresses LRP5. The method includes the step of contacting the mammary tumor cell with an agent that inhibits LRP5 activity in an amount sufficient to inhibit the proliferation or causing the death of the mammary tumor cell. Preferably, the mammary tumor cell expresses a high level of LRP5. For example, the mammary tumor cell can be a mammary tumor stem cell. Since mammary tumor stem cells are expected to co-localize with the fraction of high level LRP5 mammary tumor cells, mammary tumor stem cells can be treated by contacting a population of mammary tumor cells that express a high level of LRP5.

In one embodiment, the above method is used to treat a mammary tumor in a mammal (e.g., a human, mouse, or rat) in vivo by administering an agent that inhibits LRP5 activity into the mammal in an amount sufficient to inhibit the proliferation or causing the death of mammary tumor cells such as mammary tumor stem cells. As mammary tumor stem cells express a high level of LRP5, the method is especially useful to inhibit the growth or causing the death of mammary tumor stem cells. Optionally, another mammary tumor/breast cancer therapeutic agent such as a chemotherapeutic agent or radiation is administered in connection with the agent that inhibits LRP5 activity. This other mammary tumor/breast cancer therapeutic agent in some cases may eradicate the non-stem cell population in the mammary tumor.

One example of agents that inhibit LRP5 activity is an anti-LRP5 antibody (e.g., specific for LRP5). As LRP5 is a cellular surface receptor with an extracellular domain, an anti-LRP5 antibody directed to an epitope in the extracellular domain can readily inhibit the activity of LRP5.

In some instances, the antibody belongs to a sub-type that activates serum complement when complexed with the transmembrane protein thereby mediating cytotoxicity or antigen-dependent cytotoxicity (ADCC).

The LRP5 antibody can also be conjugated to a mammary tumor/breast cancer therapeutic agent (e.g., a chemotherapeutic agent) to deliver the therapeutic agent to the targeted tumor cells. In this case, the LRP5 antibody serves as a delivering vehicle. The therapeutic agent can be conjugated to the antibody either covalently, through a linker or a chemical bond, or noncovalently, through ionic, van der Waals, electrostatic, or hydrogen bonds. The therapeutic agent is typically a cytotoxic agent that can cause the death of the target cell.

Another example of the agents that inhibit LRP5 activity is a nucleic acid molecule that inhibits LRP5 gene expression. Examples of such nucleic acid molecules include antisense oligonucleotides, RNA interference (RNAi) molecules such as siRNA (small interfering RNA) molecules, and shRNA (short hairpin RNA) molecules. Given the cDNA sequences of LRP5 for various species are known in the art, it is well within the capability of a skilled artisan to develop such nucleic acid molecules. Both non-viral and viral vector delivery systems can be used to deliver the nucleic acid molecules. For a review of gene therapy procedures, see Anderson, Science 1992, 256:808-813; Nabel & Felgner, TIBTECH 1993, 11:211-217; Mitani & Caskey, TIBTECH 1993, 11:162-166; Dillon, TIBTECH 1993, 11:167-175; Miller, Nature 1992, 357:455-460; Van Brunt, Biotechnology 1988, 6:1149-1154; Vigne, Restorative Neurology and Neuroscience 1995, 8:35-36; Kremer & Perricaudet, British Medical Bulletin 1995, 51:31-44; Haddada et al., in Current Topics in Microbiology and Immunology Doerfler and Bohm (eds) (1995); and Yu et al., Gene Therapy 1994, 1:13-26.

In some embodiments, small interfering RNAs are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, Nature 2001, 411:428-29; Elbahir et al., Nature 2001, 411:494-98; and Fire et al., Nature 1998, 391:806-11, where methods of making interfering RNA also are discussed. The siRNA inhibitors are less than 100 base pairs, typically 30 bps or shorter, and are made by approaches known in the art. Exemplary siRNAs according to the invention can have up to 29 bps, 25 bps, 22 bps, 21 bps, 20 bps, 15 bps, 10 bps, 5 bps or any integer thereabout or therebetween.

Methods of non-viral delivery of nucleic acid molecules include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Delivery can be to cells (ex vivo administration) or target tissues (in vivo administration). The preparation of lipid:nucleic acid complexes, including targeted liposomes such as immunolipid complexes, is well known to one of ordinary skill in the art (see e.g., Crystal, Science 1995, 270:404-410; Blaese et al., Cancer Gene Ther. 1995, 2:291-297; Behr et al., Bioconjugate Chem. 1994, 5:382-389; Remy et al., Bioconjugate Chem. 1994, 5:647-654; Gao et al., Gene Therapy 1995, 2:710-722; Ahmad et al., Cancer Res. 1992, 52:4817-4820; and U.S. Pat. Nos. 4,186, 183, 4,217,344, 4,235,871, 4,261,975, 4,485,054, 4,501,728, 4,774,085, 4,837,028, and 4,946,787).

The use of RNA or DNA viral based systems for the delivery of the nucleic acid molecules are known in the art. Conventional viral based systems for the delivery of such nucleic acid molecules include retroviral, lentivirus, adenoviral, adeno-associated and herpes simplex virus vectors for gene transfer.

It may be desirable that the gene therapy vector be delivered with a high degree of specificity to a particular tissue type such as mammary tumor. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., Proc Natl Acad Sci USA 1995, 92:9747-9751, reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient (include humans and other mammals such as mice and rats), typically by systemic administration (e.g., intravenous, intraperitoneal, intramuscular, subdermal, or intracranial infusion) or topical application, as described below.

Vectors (e.g., retroviruses, adenoviruses, liposomes, etc.) containing therapeutic nucleic acids can also be administered directly to the patient for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington's Pharmaceutical Sciences, 17th ed., 1989).

The agents that inhibit LRP5 activity can be administered by a variety of methods including, but not limited to parenteral (e.g., intravenous, intramuscular, intradermal, intraperitoneal, and subcutaneous routes), topical, oral, local, or transdermal administration. These methods can be used for prophylactic and/or therapeutic treatment.

The compositions for administration will commonly comprise an agent that inhibits LRP5 activity dissolved in a pharmaceutically acceptable carrier, preferably an aqueous carrier. A variety of aqueous carriers can be used, e.g., buffered saline and the like. These solutions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions containing agents that inhibit LRP5 activity (e.g., antibodies) can be administered for therapeutic or prophylactic treatments. In therapeutic applications, compositions are administered to a patient suffering from breast cancer/mammary tumor in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents to effectively treat the patient. An amount of an agent that is capable of preventing or slowing the development of breast cancer in a patient is referred to as a "prophylactically effective dose." The particular dose required for a prophylactic treatment will depend upon the medical condition and history of the patient as well as other factors such as age, weight, gender, administration route, efficiency, etc. Such prophylactic treatments may be used, e.g., in a patient who has previously had breast cancer/mammary tumor to prevent a recurrence of the cancer/tumor, or in a patient who is suspected of having a significant likelihood of developing breast cancer/mammary tumor.

In another aspect, the present invention relates to a method for detecting or imaging mammary or mammary tumor cells that express a high level of LRP5 such as somatic mammary stem cells and mammary tumor stem cells. The method includes the steps of administering an LRP5 antibody based contrast agent and obtaining an image of the labeled mammary or mammary tumor cells. This method is useful for monitoring the effectiveness of breast cancer treatment by determining whether the mammary tumor stem cells have been inhibited or eradicated. Any suitable medical imaging techniques can be used in this regard. Examples of such techniques include ultrasound, computerized tomography (CT), magnetic resonance imaging (MRI), and nuclear medicine techniques such as gamma ray detection by a gamma ray detector (e.g., a gamma scintillation camera or a 3-dimensional imaging camera), positron emission tomography (PET) and single photon emission computed tomography (SPECT). A skilled artisan can readily make the suitable contrast agents using the LRP5 antibody, for example, by attaching a detectable label for a particular imaging technique to a LRP5 antibody (e.g., covalently through a linker or a chemical bond). For example, for MRI detection, a superparamagnetic iron oxide nanoparticle (SPION) can be conjugated to an LRP5 antibody for administering and MRI detection. For nuclear medicine detection, radionuclide-labeled LRP5 antibody can be administered and radiation emission from the nucleotide can be measured and an image thereof can be obtained.

In another aspect, the present invention relates to a method of determining breast cancer prognosis. By prognosis, we mean (i) whether a breast cancer patient is likely to survive for 5 years from initial diagnosis and be breast cancer free at the time point of 5 years from initial diagnosis or (ii) whether a breast cancer patient is likely to be metastasis-free for the period from initial diagnosis to the 5-year anniversary time point of initial diagnosis. The method involves the steps of determining the level of Lrp5 expression in breast cancer cells of a breast cancer patient and comparing the Lrp5 level of the patient to a suitable control wherein, on average, breast cancer patients with an Lrp5 level lower than the suitable control are more likely to survive for 5 years from initial diagnosis and be breast cancer free at the time point of 5 years from initial diagnosis than breast cancer patients with an Lrp5 level higher than the suitable control. Likewise, on average, breast cancer patients with an Lrp5 level lower than the suitable control are more likely to be metastasis-free for the period from initial diagnosis to the 5-year anniversary time point of initial diagnosis than breast cancer patients with an Lrp5 level higher than the suitable control.

Although Example 4 below showed that Lrp5 is useful as a breast cancer prognostic marker at the mRNA level, it is expected that LRP5 protein level can be used the same way. Therefore, Lrp5 expression level can be measured either at the mRNA level or at the protein level to practice the method of the present invention. Based on the data presented in Example 4 below, a skilled artisan can readily set up suitable controls as reference points of comparison for the expression of Lrp5. One suitable control, which is preferred, is the median or average expression level of many breast cancer patients including both patients with good prognosis and patients with poor prognosis.

Another suitable control is the median or average expression level of many breast cancer patients with poor prognosis (poor prognosis control). Still another suitable control is the median or average expression level of many breast cancer patients with good prognosis (good prognosis control). In one particular embodiment, both of the above controls are used. With these two controls, lower than good prognosis control level of Lrp5 expression indicates good prognosis and higher than poor prognosis control level of Lrp5 expression indicates poor prognosis. For example, patients with lower than good prognosis control level of Lrp5 expression will have on average a better prognosis than patients with higher than poor prognosis control level of Lrp5 expression.

The larger the number of patients used to establish a median or average level of Lrp5 expression as a control is, the more accurate the prognosis determination is. Preferably, at least 25, 50, or 100 patients are used to establish the control level of expression. In the case of using a median or average expression level of many breast cancer patients including both patients with good prognosis and patients with poor prognosis as a control, it is preferred that the number of patients with good prognosis and the number of patients with poor prognosis used to established the median or average level are about the same or within 3-fold of each other.

By way of example, but not limitation, examples of the present invention are described below.

EXAMPLE 1

The Wnt Signaling Receptor Lrp5 is Required for Mammary Ductal Stem Cell Activity and Wnt1-induced Tumorigenesis Canonical Wnt signaling has emerged as a critical regulatory pathway for stem cells. The association between ectopic activation of Wnt signaling and many different types of human cancer suggests that Wnt ligands can initiate tumor formation through altered regulation of stem cell populations. This example shows that mice deficient for the Wnt co-receptor LRP5 are resistant to Wnt1-induced mammary tumors, which have been shown to be derived from the mammary stem/progenitor cell population. These mice exhibit a profound delay in tumorigenesis that is associated with reduced Wnt1-induced accumulation of mammary progenitor cells. In addition to the tumor resistance phenotype, loss of LRP5 delays normal mammary development. The ductal trees of 5-week-old $Lrp5^{-/-}$ females have fewer terminal end buds, which are structures critical for juvenile ductal extension presumed to be rich in stem/progenitor cells. Consequently, the mature ductal tree is hypomorphic and does not completely fill the fat pad. Furthermore, Lrp5-/- ductal cells from mature females exhibit little to no stem cell activity in limiting dilution transplants. Finally, this example shows that Lrp5-/- embryos exhibit substantially impaired canonical Wnt signaling in the primitive stem cell compartment of the mammary placodes. These findings suggest that LRP5-mediated canonical signaling is required for mammary ductal stem cell activity and for tumor development in response to oncogenic Wnt effectors.

Introduction

Signaling by the Wnt family of secreted lipoproteins plays a central role in development and disease (1). At the cellular level, Wnt proteins regulate a broad range of functions, including the self-renewal and differentiation of stem cells (2). Activation of the canonical Wnt cascade is initiated by the binding of Wnt proteins to cell surface receptors composed of a member of the Frizzled protein family and one of the low density lipoprotein receptor-related proteins, LRP5 or LRP6 (3, 4). Signaling from Wnt receptors increases cytoplasmic levels of β-catenin, which binds to transcription factors such as those of the LEF-1/TCF family and modulates the transcription of specific target genes. Whereas Wnt-Frizzled interactions may also be involved in non-canonical Wnt signaling events, the LRP5/6 moiety appears to be specifically required for the canonical pathway (5).

Studies in mice suggest that canonical Wnt signaling plays a significant role during normal mammary gland development (6-11), which begins at about embryonic day 10.5 with the formation of two "mammary lines" (12). In response to signals from the underlying mesenchyme, the mammary lines give rise to five pairs of lens-shaped mammary placodes that grow and invaginate downwards into the dermis to colonize the rudimentary fat pad. Activation of the canonical Wnt signaling pathway along the mammary lines coincides with the initiation of mammary morphogenesis and subsequently localizes to mammary placodes and buds (13, 14). Several Wnt ligands and receptor genes, including Lrp5, are expressed during embryonic mammary morphogenesis (13). Embryos ectopically expressing the canonical Wnt inhibitor Dkk1 display a complete block in the formation of mammary placodes, and mice deficient for Lef-1 fail to maintain their mammary buds (6, 7), showing that Wnt signals are necessary for embryonic mammary development.

By birth, the mammary gland is composed of a few rudimentary ducts, containing an outer layer of myoepithelial and an inner layer of luminal epithelial cells, surrounded by the fat pad. During pre-pubertal and pubertal development, the ductal epithelium proliferates until the fat pad is fully colonized with a sparse ductal tree. Lobuloalveolar precursor cells respond to endocrine signals during pregnancy to colonize all the interductal spaces, increasing cell number at least 10-fold (15). The expansion of mammary epithelium during juvenile growth, estrous, and pregnancy, together with the remarkable regenerative capacity apparent during successive reproductive cycles, imply the existence of a mammary stem cell. In fact, stem-like cells from mature mammary glands have been isolated, and their ability to reconstitute the different epithelial lineages in vitro and functional ductal trees through limiting dilution transplants in vivo has been demonstrated (16, 17). However, the signals that regulate mammary stem cells have yet not been defined.

A connection between mammary stem/progenitor cells and Wnt1- or β-catenin-induced tumorigenesis has recently been established. Transgenic expression of these genes results in widespread mammary hyperplasia and rapid tumor formation (11, 18). The hyperplastic tissue contains an increased fraction of mammary stem/progenitor cells that are thought to directly give rise to transformed cells (17, 19, 20). Tumors arising from stem/progenitor cells often show mixed lineage differentiation (21), and tumors induced by Wnt effectors indeed contain cells from both epithelial lineages (19, 20).

Materials and Methods

Mouse Crosses: The Lrp5$-/-$ mice (22) (maintained on a B6 background) carry a mutation in the first exon, eliminating the initiating ATG and the sequence encoding the signal peptide. MMTV-Wnt1 transgenic mice (18) (maintained on a FVB/N background) and BAT-gal transgenic mice (23) (maintained on a B6D2FI background) were crossed with Lrp5$^{-/-}$ mice to generate Lrp5+/+, Lrp5+/-, or Lrp5-/- female mice that either carried or lacked the MMTV-Wnt1 or the BAT-gal transgene. PCR-based strategies were then used to genotype these mice. All experiments performed were in compliance with the guiding principles of the "Care and Use of Animals" available at www.nap.edu/books/0309053773/html and were approved in advance by the Van Andel Research Institute Institutional Animal Care and Use Committee. To assay the appearance of mammary tumors, the mice were inspected weekly and were euthanized when tumors appeared.

Immunohistochemistry and Western Blotting: Mammary tissues were fixed for 2 h in 4% paraformaldehyde at 4° C. and then embedded in paraffin and sectioned (5 µm). Immunohistochemistry was performed by using Vector ABC and DAB kits according to the manufacturer's recommendations (Vector Laboratories). The following primary antibodies were used: rabbit polyclonal antibody against keratin 6 (1:100; Covance), LRP5 (1:5,000; provided by John Robinson (24)), Lrp6 (1:250; Zymed Laboratories Inc.), and p21$^{CIP1}$ (1:250; Santa Cruz). Western blotting using goat polyclonal antibodies against Wnt1 (1:500; Santa Cruz) was performed as previously described in reference 19.

Mammary Whole Mounts and Analysis of BAT-Gal Expression: Inguinal mammary glands were fixed in 4% paraformaldehyde, washed in phosphate-buffered saline and stained with carmine alum, dehydrated, and cleared in xylene. For analysis of BAT-gal expression whole mount embryos were fixed (0.2% glutaraldehyde, 1.5% formaldehyde, 5 mM EGTA, 2 mM $MgCl_2$ in phosphate-buffered saline) and stained with X-gal (1 mg/ml X-gal, 2 mM $MgCl_2$, 0.01% sodium deoxycholate, 0.02% Nonidet P-40, 5 mM $Fe_3(CN)_6$, 5 mM $Fe_4(CN)_6$ in phosphate-buffered saline), photographed and paraffin-embedded, sectioned (5 µm), and counterstained with eosin. Embryonic stage was confirmed by analysis of limb morphology.

Preparation of Mammary Epithelial Cells: Mammary epithelial cells were isolated as described in reference 16. Briefly, mammary glands were digested for 8 h at 37° C. in EpiCult-B with 5% fetal bovine serum, 300 units/ml collagenase, and 100 units/ml hyaluronidase. After vortexing and lysis of the red blood cells in $NH_4Cl$, a single-cell suspension was obtained by sequential dissociation of the fragments by gentle pipetting for 1-2 min in 0.25% trypsin and then for 2 min in 5 mg/ml Dispase II plus 0.1 mg/ml DNase I, followed by filtration through a 40-mm mesh. All reagents were from StemCell Technologies Inc.

Transplantation of Cleared Mammary Fat Pads: Mammary glands of 3-week-old female B6 mice were cleared of endogenous epithelium as described in reference 25. Viable mammary epithelial cells from 2- to 3-month-old Lrp5+/+ or Lrp5-/- virgin female B6 mice were counted and suspended in Dulbecco's modified Eagle's medium plus 2% fetal bovine serum with 5 µg/ml Matrigel (BD Biosciences) at 4° C. together with loading dye (final concentration, 5% glycerol/ 0.5% trypan blue/25 mM HEPES), and inoculated in a 1-µl volume containing 500-50,000 cells/µl. Three to five months after transplantation, the fat pads were dissected, processed, and stained with carmine as described above.

Results

Lrp5Deficiency Inhibits MMTV-Wnt1-induced Carcinogenesis: Female Mice expressing the Wnt1 gene under the control of the mouse mammary tumor virus (MMTV)-long terminal repeat enhancer reproducibly develop adenocarcinomas within one year (18). To test whether LRP5 is the principal signaling receptor for Wnt ligands in mammary epithelial cells, we crossed Lrp5$^{-/-}$ mice to MMTV-Wnt1 transgenic mice. These crosses gave rise to females of approximately the same genetic background that were hemizygous for the Wnt1 transgene in the context of Lrp5$^{+/+}$, Lrp5$^{+/-}$, and Lrp5$^{-/-}$ genotypes. Wnt1 transgenic mammary tissue and tumors normally express LRP5 and LRP6 (immunohistochemical staining study). In particular, immunohistochemical stainings using an LRP5-specific polyclonal antibody showed that LRP5 is expressed in Wnt1-induced tumors and in a fraction of mammary ductal cells from hyperplastic Wnt1 transgenic mammary gland (FIGS. 1A and 1B). No staining was observed in Wnt1;Lrp5$^{-/-}$ mammary ductal cells (FIG. 1C). Immunohistochemical stainings using an Lrp6-specific polyclonal antibody showed that Lrp6 is expressed in Wnt1-induced tumors and in a fraction of mammary ductal cells from hyperplastic Wnt1 transgenic mammary gland. No staining was observed in Lrp6$^{-/-}$ embryos, which were used as negative controls because Lrp6$^{-/-}$ pups die shortly after birth. The presence or absence of LRP5 did not affect expression of the Wnt1 transgene (FIG. 1D).

We found that within 10 months, 100% of Lrp5$^{+/+}$ mice developed tumors with a median time of onset of 25 weeks, and 68% of Lrp5$^{+/-}$ mice formed tumors with a median time of onset of 35 weeks (FIG. 1E). Thus, tumor appearance was delayed several weeks in Lrp5$^{+/-}$ mice (p=3×10$^{-5}$), indicating that the gene dose of Lrp5 affects the onset of tumorigenesis. In sharp contrast, 100% of Lrp5$^{-/-}$ mice were tumor free at 10 months of age (FIG. 1E), demonstrating that absence of LRP5 suppressed tumor formation. We extended this analysis over two years and found that Lrp5$^{-/-}$ mice formed tumors with a median time of 90 weeks. Three Lrp5$^{-/-}$ mice (12%)

failed to develop palpable tumors and were sacrificed at the end of the study (124 weeks old). All mammary glands from these animals exhibited epithelial hyperplasia, but no foci of mammary tumors were found.

Histopathological examination of the tumors in this study revealed that all Lrp5$^{+/+}$ and Lrp5$^{+/-}$ tumors, as well as 18/26 Lrp5$^{-/-}$ tumors, were moderately differentiated alveolar mammary adenocarcinomas. Alveolar adenocarcinoma is the most common type of mammary tumor reported in Wnt1 transgenic mice. Five Lrp5$^{-/-}$ tumors were papillary adenocarcinomas, a morphological variant that is more differentiated and less aggressive than alveolar adenocarcinoma and normally occurs at a low frequency in Wnt1 transgenic mice (26). Hence, even though we could only detect the papillary growth pattern in Lrp5$^{-/-}$ tumors, the Lrp5$^{-/-}$ tumors were not of a different tumor type than previously described for Wnt1-induced tumors. Furthermore, all tumors regardless of Lrp5 genotype expressed cell markers from both the myoepithelial and the luminal epithelial cell lineages, and all tumors contained cells positive for the putative mammary progenitor cell marker keratin 6 (19). Taken together, these findings suggest that the tumor precursor cell is likely the same regardless of Lrp5 genotype.

Figure 2:
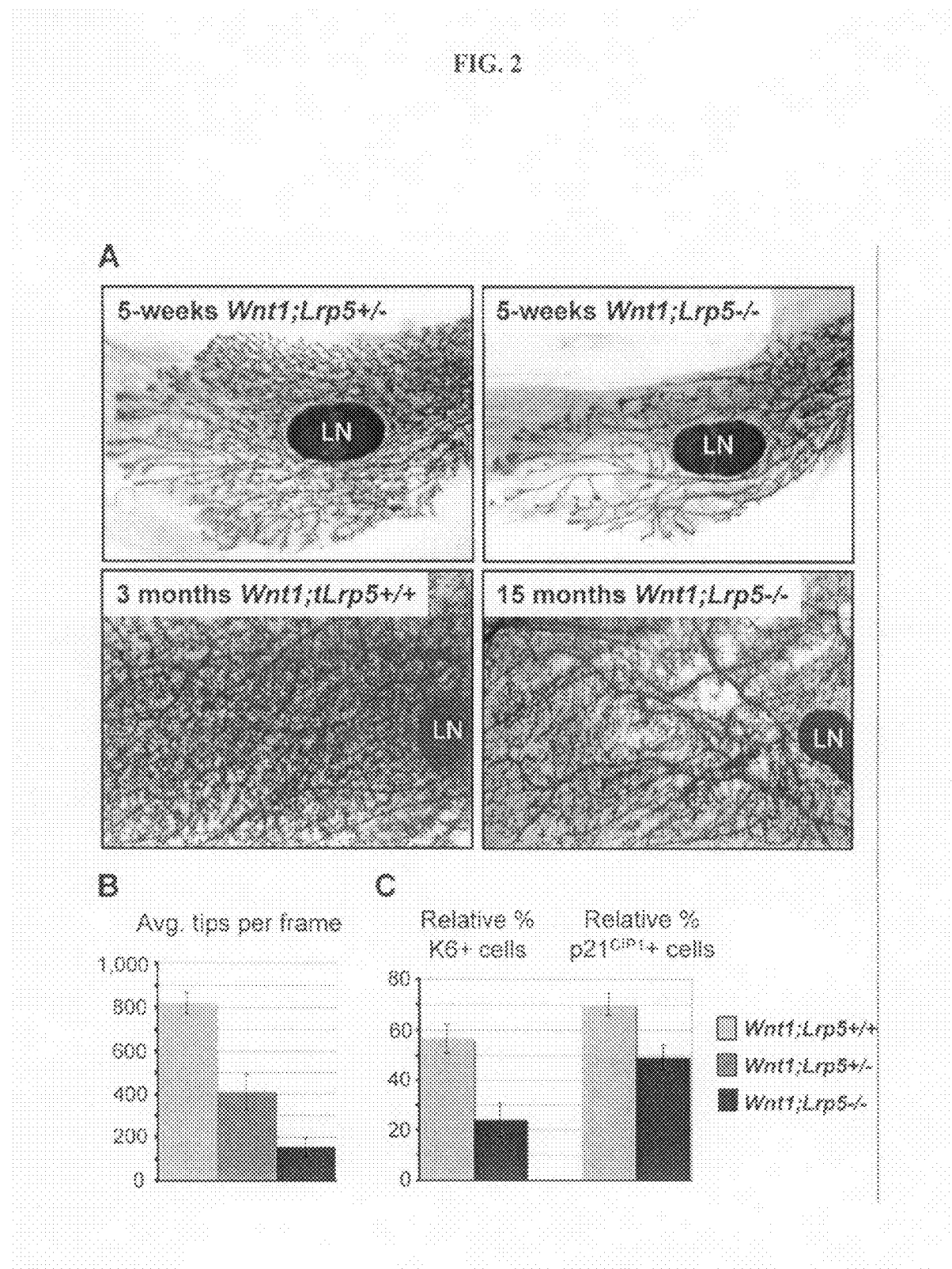
FIG. 2 shows that the absence of Lrp5 delays Wnt1-induced mammary hyperplasia and reduces the accumulation of keratin 6- and p21$^{CIP1}$-positive cells. A, hyperplastic side branching characteristic of MMTV-Wnt1 transgenic mice throughout development is inhibited in Lrp5$^{-/-}$ mammary glands. Representative whole mount preparations (stained with carmine to reveal the mammary ductal tree) are shown for juvenile mice (5-week) and mature virgin female mice. LN, lymph node. B, morphometric analysis of carmine-stained mammary glands from 3-month-old MMTV-Wnt1 transgenic females. The same area of each inguinal mammary gland was scored for the number of tips (ends of branches and lateral buds) from four MMTV-Wnt1 mice of each Lrp5 genotype. The number of tips is reduced by 80% in Wnt1; Lrp5$^{-/-}$ mammary glands compared with Wnt1;Lrp5$^{+/+}$ control glands (p=6.5×10$^{-6}$, 2-tailed t test assuming unequal variances). Immunohistochemical staining of Lrp5$^{+/+}$ and Lrp5$^{-/-}$ MMTV-Wnt1 mammary samples from 11-week-old females was used to determine the number and distribution of cells positive for mammary progenitor cell marker keratin 6. The average number of keratin 6-positive cells per total number of ductal cells is shown in panel C. Wnt1;Lrp5$^{-/-}$ ducts contained 58% fewer keratin 6-positive cells (p=2.8×10$^{-6}$, 2-tailed t test assuming unequal variances). The same counting strategy was used for p21$^{CIP1}$. C, Lrp5$^{+/+}$ and Lrp5$^{-/-}$ MMTV-Wnt1 mammary samples from 5-week-old females were used for the morphometric analysis of p21$^{CIP1}$. Wnt1; Lrp5$^{-/-}$ ducts contained 30% fewer p21$^{CIP1}$-positive cells (p=0.0044, 2-tailed t test assuming unequal variances).

Loss of Lrp5 Delays Wnt1-induced Mammary Hyperplasia: Tumors induced by Wnt effectors ultimately arise within a context of widespread mammary hyperplasia that is noticeable as early in development as embryonic day 18 (18). To determine the contribution of LRP5 to Wnt1-induced mammary gland hyperplasia, ductal development was analyzed in virgin MMTV-Wnt1;Lrp5$^{-/-}$ mice. Inguinal mammary glands were isolated, whole mounted, and compared in the juvenile (5-week) and mature (3 and 15-month) mammary glands from MMTV-Wnt1;Lrp5$^{-/-}$ and control female mice. In the absence of LRP5, we found that the hyperplastic response to Wnt1 was dramatically delayed (FIG. 2A). Morphometric analysis showed that hyperplasia was inhibited by 80% in mammary glands from Lrp5$^{-/-}$ mice relative to Lrp5$^{+/+}$ matched controls (p=6.5×10$^{-6}$) (FIG. 2B).

The hyperplastic mammary tissue of Wnt1 transgenic mice contains an increased ratio of mammary progenitor cells (17, 19, 20). These progenitor cells are thought to directly give rise to transformed cells. To test whether the delay in tumorigenesis could be due to a reduced accumulation of mammary progenitor cells, we immunostained mammary sections from MMTV-Wnt1;Lrp5$^{-/-}$ and control female mice using keratin 6 antibody. We found that Wnt1 transgenic mammary ducts from Lrp5$^{-/-}$ females contained less than half the number of keratin 6-positive cells detected in littermate controls (FIG. 2C). This was further confirmed by staining for another putative mammary progenitor cell marker, p21$^{CIP1}$ (27), which also showed a significant reduction of positive cells in Lrp5$^{-/-}$ ducts (FIG. 2C). Taken together, these findings suggest that Lrp5 deficiency reduces the normal accumulation of mammary stem and progenitor cells in MMTV-Wnt1 transgenic mice.

Impaired Mammary Gland Development in Lrp5$^{-/-}$ Mice: To determine the contribution of LRP5 to normal mammary gland function, ductal development was analyzed in virgin Lrp5$^{-/-}$ mice. Whole mount preparations of inguinal mammary glands are shown for juvenile (5-week) and mature (11-week) mammary glands from Lrp5$^{-/-}$ and control female littermates (FIG. 3A). At 5 weeks the ductal network extends away from the nipple through the fat pad, past the lymph node. The mammary ducts of Lrp5$^{-/-}$ mice were clearly shorter than those of littermate controls. Whereas the Lrp5$^{-/-}$ ductal tree ended right around the lymph node, the wild type had extended considerably further. Terminal end buds (TEBs) are club-shaped epithelial thickenings at the distal ends of growing ducts and are the sites of most rapid cell proliferation and ductal elongation. TEBs are presumed to be rich in mammary stem cells (28, 29). We found that the number of TEBs was reduced by 42% in juvenile Lrp5$^{-/-}$ mice compared with littermate wild-type mice (p=0.0003) (FIG. 3B). In both control and Lrp5$^{-/-}$ mice, the histology of the TEBs appeared normal.

The branching complexity in adult mice is a function of terminal end bud activity during juvenile ductal extension. TEBs normally disappear when the ductal tree is fully branched and fills the fat pad. In contrast, the ductal tree of adult Lrp5$^{-/-}$ mice still contained TEBs and did not completely fill the mammary fat pad (FIG. 3A). Morphometric analysis showed that the branching complexity of adult Lrp5$^{-/-}$ glands was decreased by 46% compared with littermate wild-type mice (p=0.001) (FIG. 3C). On the histological level, the adult Lrp5$^{-/-}$ mammary glands looked normal except for the reduction of mammary ducts as seen on whole mounts.

Epithelial Transplants from Lrp5$^{-/-}$ Mice Lack Stem Cell Activity: The outgrowth of a full mammary branching tree from limiting dilutions of mammary epithelial cell transplants is considered to be an assay of clonal stem cell function (25). Surgical removal of the area between the nipple and the fat pad at 3 weeks of age leaves a fat pad free of the endogenous mammary epithelium. Mammary cells from another syngenic animal can be implanted and will develop an epithelial tree if the transplant contains cells with stem cell activity. One benefit of this technique is that the transplanted cells are exposed to normal circulating hormone levels and wild-type stroma. To test whether the reduction in terminal end bud numbers and branching complexity of Lrp5-/- mammary glands could be due to compromised mammary stem cell activity, we transferred cells from 12- to 15-week-old Lrp5$^{-/-}$ and wild-type glands by limiting dilutions (500-50, 000) into cleared fat pads of 3-week-old congenic or isogenic recipients. Transplants were harvested after 3-5 months, and whole mounts were prepared to evaluate the extent of epithelial outgrowth. Half and 32% of host glands were colonized after the transfer of 5,000 and 500 wild-type mammary cells, respectively (FIG. 4A). Only one of 46 fat pads hosting Lrp5$^{-/-}$ mammary cells contained a mammary tree (FIG. 4A); an additional three host glands contained an epithelial rudiment. In fact, transfers of 50,000 Lrp5$^{-/-}$ mammary cells still failed to reconstitute a mammary tree (FIGS. 4, A and B), suggesting a loss of stem cell activity in the context of LRP5 deficiency.

Canonical Wnt Signaling Is Compromised in Lrp5$^{-/-}$ Mammary Placodes: Mammary development begins at E10.5, and by birth a primitive ductal tree has formed. The stem cells required for its extension during puberty are already present at birth. To test whether LRP5 is the principal signaling receptor for Wnt ligands during embryonic mammary development, we crossed Lrp5$^{-/-}$ mice to transgenic mice carrying a BAT-gal lacZ reporter gene that is expressed at sites of canonical pathway activity (23). Reporter gene activity, detected by X-gal staining for β-galactosidase, was significantly reduced in Lrp5$^{-/-}$ embryos relative to littermate controls. In particular, at E12.5 X-gal staining reveals that the mammary placodes stain dark blue in embryos that carry at least one copy of Lrp5. In Lrp5$^{-/-}$ BAT-gal transgenic embryos the staining of the mammary placodes is significantly fainter. On the histological level the mammary placodes of Lrp5$^{-/-}$ embryos were significantly smaller and contained fewer cells with reporter gene activity than mammary placodes from littermates carrying at least one intact copy Lrp5. We also performed X-gal staining on mammary whole mounts from newborn, juvenile, and adult virgin females. Reporter gene activity was significantly reduced in the ductal tree of 2-day-old Lrp5$^{-/-}$ female mice relative to littermate controls (both in regard to staining intensity and to the number of BAT-gal-positive cells). BAT-gal expression could not be detected after the first week of life, which is consistent with previous reports (13, 14).

In summary, we described in the above study a requirement for the Wnt co-receptor LRP5 in mammary morphogenesis and tumor formation mediated by ductal stem cells. Importantly, Lrp5$^{-/-}$ mice are resistant to Wnt1-induced tumors, which have been shown to be derived from the mammary stem/progenitor cell population. These mice exhibit a profound delay in tumorigenesis that is associated with reduced Wnt1-induced hyperplasia and reduced accumulation of mammary progenitor cells. In addition to the tumor resistance phenotype, loss of Lrp5 impairs various stem cell activities required for normal mammary development, and Lrp5$^{-/-}$ ductal cells exhibit little to no stem cell activity in limiting dilution transplants. Lrp5$^{-/-}$ embryos also exhibit substantially impaired canonical Wnt signaling in the primitive stem cell compartment of the mammary placode. Lrp5$^{-/-}$ mice still express Lrp6 throughout mammary development (data not shown), and the Wnt1-induced tumors that finally do arise in Lrp5$^{-/-}$ mice also express Lrp6. Non-canonical Wnt signaling or mTOR signaling directly induced by Wnt ligands may also play a role in Wnt1-induced tumorigenesis and contribute to tumor development in Lrp5$^{-/-}$ mice (30, 31). These findings have important implications for the characterization of mammary stem cells and tumors induced by Wnt effectors.

Canonical Wnt signaling has been implicated in the regulation of various stem cells, including hematopoietic, intestinal, and epidermal stem cells (32). For example, soluble Wnt proteins promote growth and inhibit differentiation in hematopoietic stem cells (2). Wnt signaling also inhibits the differentiation of stem cells in the intestinal epithelium and in hair follicles (33, 34). In many of the same tissues where the Wnt pathway controls stem cells, deregulation of Wnt signaling leads to tumor formation. Stabilization of β-catenin in the intestinal epithelium or overexpression of β-catenin in the epidermis results in the development of intestinal adenomas or hair tumors, respectively (35, 36). This suggests that Wnt ligands can initiate tumor formation through altered regulation of stem cell populations.

The pre-neoplastic hyperplasia contains an increased fraction of cells positive for molecular markers that have been associated with mammary progenitor cells, and the likelihood of progression to carcinoma correlates with the overall number of progenitor cells (17, 19, 20). In addition, mammary ductal cells from pre-neoplastic Wnt1 transgenic mice show an increased frequency of cells with stem cell activity, measured by transferring limiting dilutions of cells to fat pads in vivo (17, 20). This finding again demonstrates the ability of the Wnt pathway to target stem/progenitor cells for transformation, possibly reflecting a role of the Wnt pathway in the self-renewal of normal breast epithelium.

It is disclosed here for the first time that loss of LRP5-mediated canonical Wnt signaling impairs the mammary stem cell compartment. During normal development, the ductal tree fills the mammary fat pad by the end of puberty and TEBs disappear. In the absence of Lrp5, juvenile ductal branching and extension is supported by fewer TEBs and is significantly delayed. TEBs persist several weeks after they disappear in control littermate females, and the ductal tree never fills the fat pad, even after the TEBs disappear. Lrp5$^{-/-}$ ductal cells are unable to reconstitute ductal trees even when transplanted in large numbers (50,000 ductal cells). Shackleton et al. (17) recently showed that a functional mammary gland could be generated from the transplantation of one ductal stem cell. They estimated the fraction of ductal stem cells in the mature mammary gland to be 1/1,400. Thus we conclude that the mammary glands from adult Lrp5$^{-/-}$ females lack functioning somatic stem cells.

Without intending to be limited by theory, there are various ways to explain why Lrp5$^{-/-}$ mammary glands are relatively normal but contain no or very few stem cells: 1) fewer primitive mammary stem cells develop leading to very low stem cell fractions in the adult mammary gland; 2) the proportion of stem cells dividing by self-renewal (and symmetric division) is decreased, leading to progenitor-based organogenesis (either because the stem cell niche is ineffective or the cells differentiate precociously); or 3) canonical Wnt signaling is required for stem/progenitor cell survival (37). In support of 1), our analysis of Wnt reporter mice shows that Lrp5$^{-/-}$ embryos develop abnormally small mammary placodes with significantly reduced canonical signaling relative to littermate controls. Previous literature on Wnt reporter mice has shown that canonical Wnt signaling is specifically active during embryonic mammary development (13, 14). Furthermore, Wnt signaling is absolutely required, because mammary placodes fail to develop in transgenic mice overexpressing the Wnt inhibitor Dkk1 (6). Dkk1 inhibits the Wnt signaling pathway by binding to, and presumably inactivating, LRP5 and LRP6.

A growing body of evidence suggests that specific subtypes of the most common human tumors, including breast (38), lung (39), and colon (40), originate in stem cell compartments. Signaling pathways that regulate stem cell activity could therefore be effective drug targets. In fact, several studies have shown that activation of canonical Wnt signaling is common in human breast cancer (41-43). We show that in the absence of LRP5, the response to ectopically expressed Wnt1 in the mammary epithelium is almost eliminated, as is tumor development.

REFERENCES

1. Nusse, R. (2005) *Cell Res.* 15, 28-32.
2. Reya, T., Duncan, A. W., Ailles, L., Domen, J., Scherer, D.C., Willert, K., Hintz, L., Nusse, R., and Weissman, I. L. (2003) *Nature* 423, 409-414.
3. Sharpe, C., Lawrence, N., and Martinez Arias, A. (2001) *BioEssays* 23, 311-318.
4. Schweizer, L., and Varmus, H. (2003) *BMC Cell Biol.* 4, 4.
5. Liu, G., Bafico, A., and Aaronson, S. A. (2005) *Mol. Cell. Biol.* 25, 3475-3482.
6. Andl, T., Reddy, S. T., Gaddapara, T., and Millar, S. E. (2002) *Dev. Cell* 2, 643-653.
7. van Genderen, C., Okamura, R. M., Farinas, I., Quo, R. G., Parslow, T. G., Bruhn, L., and Grosschedl, R. (1994) *Genes Dev.* 8, 2691-2703.
8. Hsu, W., Shakya, R., and Costantini, F. (2001) *J. Cell Biol.* 155, 1055-1064.
9. Brisken, C., Heineman, A., Chavarria, T., Elenbaas, B., Tan, J., Dey, S. K., McMahon, J. A., McMahon, A. P., and Weinberg, R. A. (2000) *Genes Dev.* 14, 650-654.
10. Tepera, S. B., McCrea, P. D., and Rosen, J. M. (2003) *J. Cell Sci.* 116, Pt. 6, 1137-1149.
11. Imbert, A., Eelkema, R., Jordan, S., Feiner, H., and Cowin, P. (2001) *J. Cell Biol.* 153, 555-568.
12. Veltmaat, J. M., Mailleux, A. A., Thiery, J. P., and Bellusci, S. (2003) *Differentiation* 71, 1-17.

13. Chu, E. Y., Hens, J., Andl, T., Kairo, A., Yamaguchi, T. P., Brisken, C., Glick, A., Wysolmerski, J. J., and Millar, S. E. (2004) *Development* 131, 4819-4829.
14. Boras-Granic, K., Chang, H., Grosschedl, R., and Hamel, P. A. (2006) *Dev. Biol.* 295, 219-231.
15. Hennighausen, L., and Robinson, G. W. (1998) *Genes Dev.* 12, 449-455.
16. Stingl, J., Eirew, P., Ricketson, I., Shackleton, M., Vaillant, F., Choi, D., Li, H. I., and Eaves, C. J. (2006) *Nature* 439, 993-997.
17. Shackleton, M., Vaillant, F., Simpson, K. J., Stingl, J., Smyth, G. K., Asselin-Labat, M. L., Wu, L., Lindeman, G. J., and Visvader, J. E. (2006) *Nature* 439, 84-88.
18. Tsukamoto, A. S., Grosschedl, R., Guzman, R. C., Parslow, T., and Varmus, H. E. (1988) *Cell* 55, 619-625.
19. Li, Y., Welm, B., Podsypanina, K., Huang, S., Chamorro, M., Zhang, X., Rowlands, T., Egeblad, M., Cowin, P., Werb, Z., Tan, L. K., Rosen, J. M., and Varmus, H. E. (2003) *Proc. Natl. Acad. Sci. U.S.A.* 100, 15853-15858.
20. Liu, B. Y., McDermott, S. P., Khwaja, S. S., and Alexander, C. M. (2004) *Proc. Natl. Acad. Sci. U.S.A.* 101, 4158-4163.
21. Owens, D. M., and Watt, F. M. (2003) *Nat. Rev. Cancer* 3, 444-451.
22. Holmen, S. L., Giambernardi, T. A., Zylstra, C. R., Buckner-Berghuis, B. D., Resau, J. H., Hess, J. F., Glatt, V., Bouxsein, M. L., Ai, M., Warman, M. L., and Williams, B. O. (2004) *J. Bone. Miner. Res.* 19, 2033-2040.
23. Maretto, S., Cordenonsi, M., Dupont, S., Braghetta, P., Broccoli, V., Hassan, A. B., Volpin, D., Bressan, G. M., and Piccolo, S. (2003) *Proc. Natl. Acad. Sci. U.S.A.* 100, 3299-3304.
24. Babij, P., Zhao, W., Small, C., Kharode, Y., Yaworsky, P. J., Bouxsein, M. L., Reddy, P. S., Bodine, P. V., Robinson, J. A., Bhat, B., Marzolf, J., Moran, R. A., and Bex, F. (2003) *J. Bone Miner. Res.* 18, 960-974.
25. Kordon, E. C., and Smith, G. H. (1998) *Development* 125, 1921-1930.
26. Donehower, L. A., Godley, L. A., Aldaz, C. M., Pyle, R., Shi, Y. P., Pinkel, D., Gray, J., Bradley, A., Medina, D., and Varmus, H. E. (1995) *Genes Dev.* 9, 882-895.
27. Clarke, R. B., Spence, K., Anderson, E., Howell, A., Okano, H., and Potten, C. S. (2005) *Dev. Biol.* 277, 443-456.
28. Kenney, N. J., Smith, G. H., Lawrence, E., Barrett, J. C., and Salomon, D. S. (2001) *J. Biomed. Biotechnol.* 1, 133-143.
29. Williams, J. M., and Daniel, C. W. (1983) *Dev. Biol.* 97, 274-290.
30. Veeman, M. T., Axelrod, J. D., and Moon, R. T. (2003) *Dev. Cell* 5, 367-377.
31. Inoki, K., Ouyang, H., Zhu, T., Lindvall, C., Wang, Y., Zhang, X., Yang, Q., Bennett, C., Harada, Y., Stankunas, K., Wang, C. Y., He, X., Macdougald, O. A., You, M., Williams, B. O., and Guan, K. L. (2006) *Cell* 126, 955-968.
32. Reya, T., and Clevers, H. (2005) *Nature* 434, 843-850.
33. Korinek, V., Barker, N., Moerer, P., van Donselaar, E., Huls, G., Peters, P. J., and Clevers, H. (1998) *Nat. Genet.* 19, 379-383.
34. Huelsken, J., Vogel, R., Erdmann, B., Cotsarelis, G., and Birchmeier, W. (2001) *Cell* 105, 533-545.
35. Dietrich, W. F., Lander, E. S., Smith, J. S., Moser, A. R., Gould, K. A., Luongo, C., Borenstein, N., and Dove, W. (1993) *Cell* 75, 631-639.
36. Gat, U., DasGupta, R., Degenstein, L., and Fuchs, E. (1998) *Cell* 95, 605-614.
37. Paguirigan, A., Beebe, D. J., Liu, B., and Alexander, C. (2006) *Eur. J. Cancer* 42, 1225-1236.
38. Al-Hajj, M., Wicha, M. S., Benito-Hernandez, A., Morrison, S. J., and Clarke, M. F. (2003) *Proc. Natl. Acad. Sci. U.S.A.* 100, 3983-3988.
39. Kim, C. F., Jackson, E. L., Woolfenden, A. E., Lawrence, S., Babar, I., Vogel, S., Crowley, D., Bronson, R. T., and Jacks, T. (2005) *Cell* 121, 823-835.
40. Radtke, F., and Clevers, H. (2005) *Science* 307, 1904-1909.
41. Lin, S. Y., Xia, W., Wang, J. C., Kwong, K. Y., Spohn, B., Wen, Y., Pestell, R. G., and Hung, M. C. (2000) *Proc. Natl. Acad. Sci. U.S.A.* 97, 4262-4266.
42. Ugolini, F., Charafe-Jauffret, E., Bardou, V. J., Geneix, J., Adelaide, J., Labat-Moleur, F., Penault-Llorca, F., Longy, M., Jacquemier, J., Birnbaum, D., and Pebusque, M. J. (2001) *Oncogene* 20, 5810-5817.
43. Klopocki, E., Kristiansen, G., Wild, P. J., Klaman, I., Castanos-Velez, E., Singer, G., Stohr, R., Simon, R., Sauter, G., Leibiger, H., Essers, L., Weber, B., Hermann, K., Rosenthal, A., Hartmann, A., and Dahl, E. (2004) *Int. J. Oncol.* 25, 641-649.

EXAMPLE 2

LRP5 is a Biomarker for Mammary Stem Cells

Materials and Methods

Mammary glands were obtained from 14 week old, virgin Balb/c mice. The glands were harvested and minced with fine scissors on ice. Mammary organoids were dissociated by enzymatic digestion with hyaluronidase and collagenase for six hours at 37° C. (reagents and protocol from Stem Cell Technologies, Vancouver, Canada). The mammary organoids were then further dissociated into single cells by brief trypsin and dispase exposures (reagents and protocol from Stem Cell Technologies). Single mammary epithelial cell preparations were then stained with the following rat antibodies (BD Biosciences, San Jose, Calif.): anti-CD45-APC (30-F11) and anti-CD31-APC (MEC 13.3) for 30 min at 4° C. In addition, the cells were also incubated for 30 min at 4° C. with rabbit anti-mouse LRP5 (Babij P. et al. J. Bone Miner. Res. 2003, 18:960-974) followed by incubation with Goat anti-rabbit IgG-Pacific Blue (Molecular Probes, Eugene, Oreg.) for 30 min at 4° C. The cells were then analyzed using a FACSVantage cell sorter with DiVa software (BD Biosciences). Apoptotic and necrotic cells were first gated out using propidium iodide (2 µg/µl, Sigma, St. Louis, Mo.). Hematopoetic and endothelial cells were then gated out based on CD45 and CD31 staining, respectively. The remaining cells were then sorted and analyzed for LRP5 staining. Cells exhibiting either high (top 5.13%) or negative levels of LRP5 staining were subsequently sorted into polystyrene flow tubes containing pure FBS. The sorted sub-populations were stored in liquid nitrogen until transplantation into recipient mice for assaying stem cell activity. Mammary fat transplantation assay is well known in the art (see e.g., Kordon, E. C., and Smith, G. H. *Development* 1998, 125:1921-1930; and DeOme K B et al. *J. Natl. Cancer Inst.* 1959, 78:751-757).

Results

Figure 5:
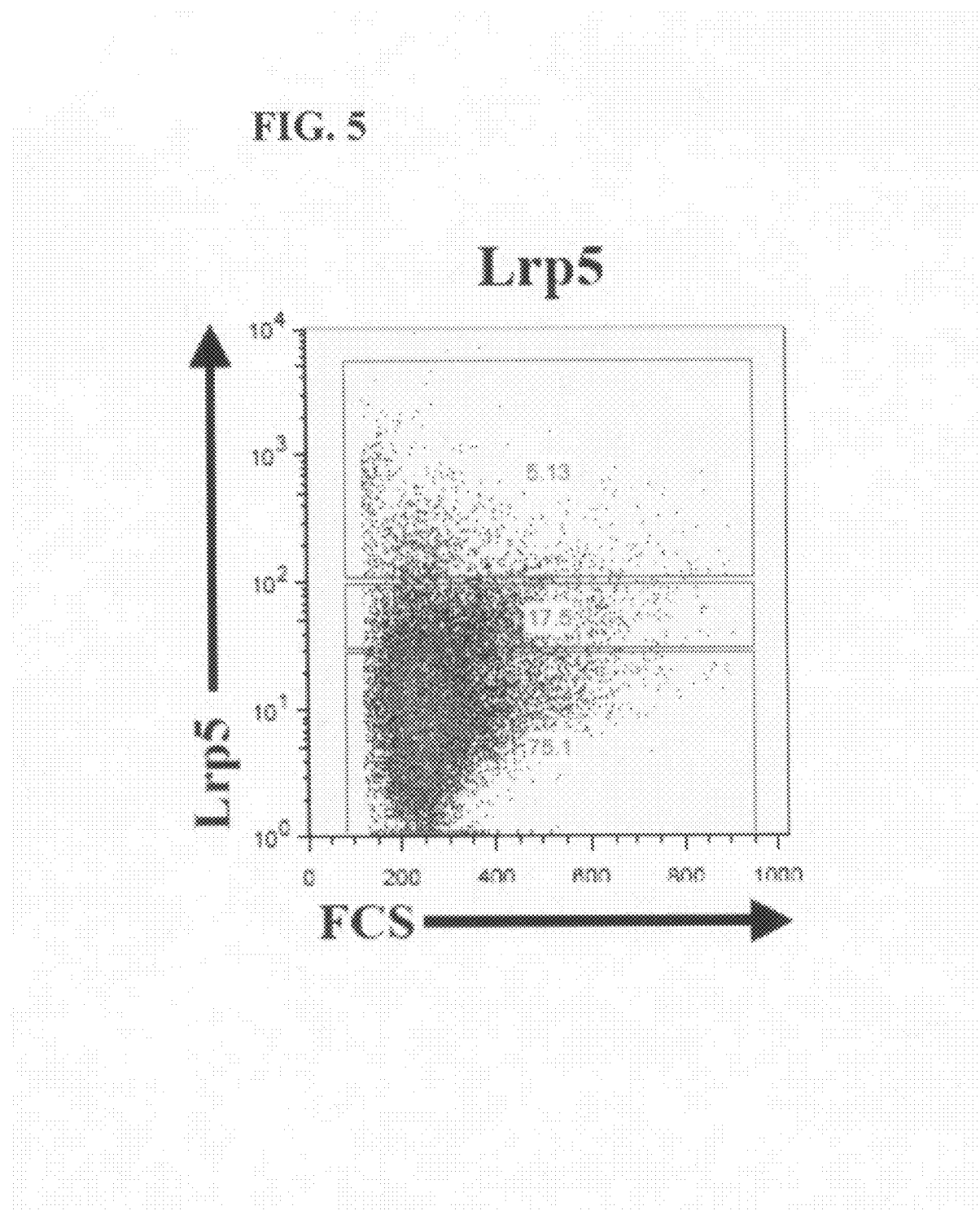
FIG. 5 is a FACS diagram of LRP5 staining. Single cell preparations of mammary epithelial cells were obtained by brief trypsin and dispase exposures (reagents and protocol from Stem Cell Technologies, Vancouver, BC, Canada). The cells were then stained with Rabbit anti-LRP5-Pacific Blue in addition to the following rat antibodies: anti-CD45-APC (30-F11) and anti-CD31-APC (MEC 13.3) for 30 min at 4° C. The cells were then analyzed using a FACSVantage cell sorter with DiVa software. Hematopoetic and endothelial cells were gated out based on CD45 and CD31 staining, respectively, prior to LRP5 analysis.

Stem Cell Activity is Augmented in Mammary Epithelial Cells with High Levels of Lrp5 Expression: Staining of mammary epithelial cells for LRP5 revealed a gradient of Lrp5 expression from negative to high levels (FIG. 5). We found that about 75% of the cells were LRP5 negative (FIG. 5). We also found that some CD31+ cells are LRP5 positive and almost all CD45+ cells are LRP5 negative. Therefore, one may only need to gate out CD31+ cells from the initially isolated mammary cells to improve the selection efficiency of LRP5 positive mammary epithelial cells or somatic mammary stem cells. To directly test the in vivo stem cell activity of LRP5 expressing mammary epithelial cells, we transplanted purified LRP5-high (top 5.13% in this particular experiment), LRP5-negative, and the total mammary epithelial cell population into cleared fat pads of 3 week old Balb/c recipient mice. The isolated mammary epithelial cell fractions were transplanted in limiting dilutions and the resulting outgrowths were scored 8 weeks following transplantation. Mammary outgrowths from the LRP5-high fraction revealed the stem cell activity of the LRP5-high cells was highly augmented (at least 10-fold) compared to the total population (FIG. 6). In addition, the LRP5-negative fraction was found to have significantly decreased stem cell activity, compared to both the total population and the LRP5-high fraction. These results show that high levels of LRP5 expression are required for normal mammary stem cell activity. Since Wnt signaling has been shown to maintain stem cell pools in other tissues, it is likely that the mammary gland also requires Wnt signaling through LRP5 to maintain the mammary stem cell pool.

EXAMPLE 3

LRP5 Expression in the Mammary Glands of Wild-type and Lrp5-null Mice as Well as MMTV-Wnt1 Transgenic Mice Methods for immunohistochemistry for Lrp5 expression: Wild-type and Lrp5-null (Lrp5−/−, negative control) female mammary glands of congenic B6 mice and mammary glands of MMTV-Wnt1 transgenic mice (Tsukamoto A S et al. *Cell* 1988, 55:619-625) were isolated and fixed in 4% paraformaldehyde in PBS at 4° C. overnight. The mammary glands were then embedded in paraffin and cut at a thickness of 5 μm. The sections were deparaffinized and rehydrated. Immunohistochemistry for LRP5 was performed using rabbit polyclonal anti-mouse antibody G171V at a dilution of 1:5000. The localization of the primary antibody was identified by biotinylated anti-rabbit IgG, amplified with ABC reagent and visualized by 3,3'-diaminobenzidine (DAB) (Vector laboratories). The sections were counterstained with hematoxyline.

Figure 7:
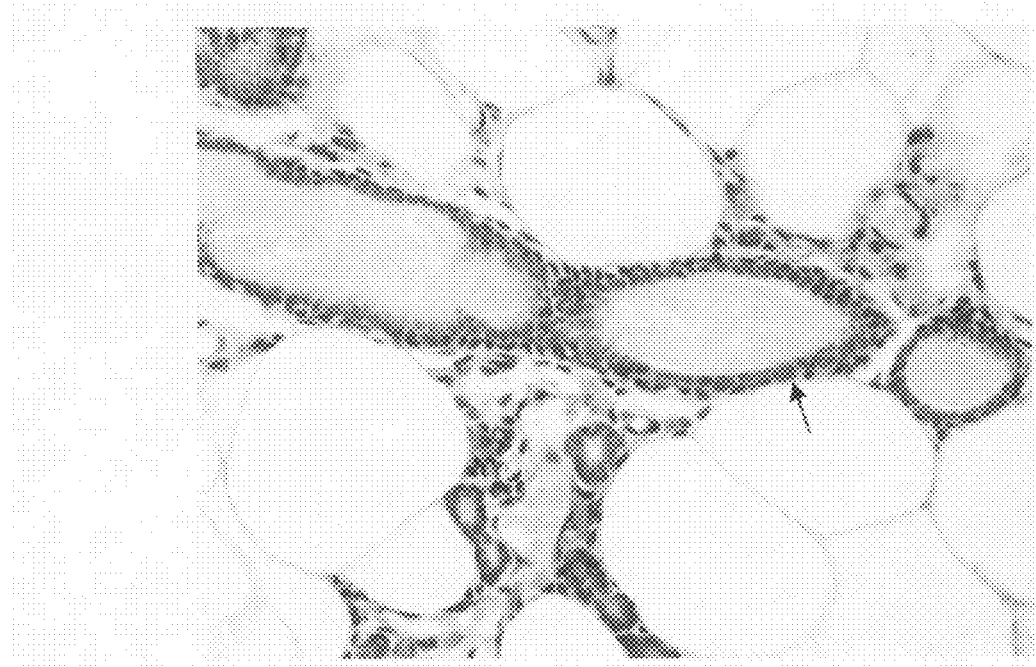
FIG. 7 shows immunohistochemical staining of adult mammary tissue of a wild-type B6 mouse using an LRP5-specific polyclonal antibody. The arrow indicates a representative cell with positive staining (brown). The tissue was counterstained with hematoxylin. Hence, cells that lack Lrp5 expression are blue. Lrp5 is found to be expressed on the cellular surface of a small fraction of mammary ductal cells. Some LRP5 staining can also be observed in the stroma surrounding the mammary ducts.

Results: FIG. 7 shows a section of mammary gland immunohistochemistry of a wild-type B6 mouse. As can be seen in FIG. 7, Lrp5 is expressed on the cellular surface of a small fraction of mammary ductal cells. The arrow indicates a representative cell with positive staining (brown). The tissue was counterstained with hematoxylin. Hence, cells that lack Lrp5 expression are blue. Some LRP5 staining can also be observed in the stroma surrounding the mammary ducts. We quantified the percentage of LRP5 positive cells per mammary ducts and found 5.6% (standard deviation 2.8%) of the ductal cells to be LRP5 positive.

As expected, no ductal cells from Lrp5-null mice stained positive for LRP5.

Immunohistochemical staining of mammary glands of MMTV-Wnt1 transgenic mice showed a similar pattern of staining as the wild-type B6 mice described above except that a higher percentage (18.4%) of LRP5 positive ductal cells was found with MMTV-Wnt1 transgenic mice. This further supports that LRP5 is a stem cell marker. The stem cell population is increased in MMTV-Wnt1 mice (Shackleton M et al. Nature 2006, 439:84-88).

EXAMPLE 4

Lrp5 Expression in Breast Cancer Cells can Serve as a Prognostic Marker

The data of a published microarray gene expression study (Van de Vijver et al. N Engl J Med. 2002, 347:1999-2009, which is herein incorporated by reference in its entirety) that included clinical outcome for many breast cancer patients were downloaded using the software Oncomine and LRP5 expression pattern was analyzed. We found that the population of breast cancer patients who still have cancer (either the original cancer or recurrence) or have died at the 5 year time point from first diagnosis expresses a higher level of LRP5 in the tumor cells at the mRNA level (the median level of expression) than the population of breast cancer patients who are cancer-free at the 5 year time point from first diagnosis (FIG. 8). Further, the population of breast cancer patients with metastasized cancer (within 5 years of initial diagnosis) expresses a higher level of LRP5 in the tumor cells at the mRNA level (the median level of expression) than the population of breast cancer patients who are metastasis-free (within 5 years of initial diagnosis) (FIG. 9). Therefore, LRP5 can serve as a prognostic marker for breast cancer.

Although the invention has been described in connection with specific embodiments, it is understood that the invention is not limited to such specific embodiments but encompasses all such modifications and variations apparent to a skilled artisan that fall within the scope of the appended claims.

We claim:

1. A method for enriching a population of mammary cells or mammary tumor cells for somatic mammary stem cells or mammary tumor stem cells, the method comprising the steps of:
   obtaining a population of mammary cells or mammary tumor cells containing one or more somatic mammary stem cells or mammary tumor stem cells;
   contacting said population of mammary cells or mammary tumor cells with an anti-low density lipoprotein receptor-related protein 5 (LRP5) antibody; and
   selecting cells that bind to the antibody.

2. The method of claim 1, wherein the population of mammary cells or mammary tumor cells is a population of human, mouse, or rat cells.

3. The method of claim 1, wherein the population of mammary cells or mammary tumor cells is a population of mouse cells.

4. The method of claim 1, wherein the mammary cell population comprises at least 70% of the total mammary epithelial cell population of a mammary gland.

5. The method of claim 1, wherein the antibody is attached to a solid matrix.

6. The method of claim 1, wherein cells that bind to the antibody are selected by flow cytometry.

7. The method of claim 6, wherein the cells are selected from the top 10% or higher of the total mammary epithelial cell population from a mammary gland in terms of LRP5 expression.

8. The method of claim 7, wherein the cells are selected from the top 6% or higher of the total mammary epithelial cell population from a mammary gland in terms of LRP5 expression.

9. The method of claim 1, wherein the method is for enriching a population of mammary cells for somatic mammary stem cells.

10. The method of claim 9 further comprising the step of contacting said population of mammary cells with an antibody against a cell surface marker for cells selected from endothelial cells, hematopoietic cells, and stromal cells wherein cells that bind to the anti-LRP5 antibody but not the antibody against the cell surface marker for cells selected from endothelial cells, hematopoietic cells, and stromal cells are selected.

11. The method of claim 9, wherein at least 1% of the selected cells are somatic mammary stem cells.

12. The method of claim 9, wherein at least 5% of the selected cells are mammary stem cells.

* * * * *

UNITED STATES PATENT AND TRADEMARK OFFICE
CERTIFICATE OF CORRECTION

PATENT NO. : 7,563,619 B2
APPLICATION NO. : 11/807937
DATED : July 21, 2009
INVENTOR(S) : Bart Williams et al.

Page 1 of 1

It is certified that error appears in the above-identified patent and that said Letters Patent is hereby corrected as shown below:

In the Specification

Column 1, Lines 12-15:
Delete the phrase:
"This invention was made with United States government support awarded by the following agency: NIH RO1 CA113869-01. The United States has certain rights in this invention."
And replace with:
--This invention was made with government support under CA090877 awarded by the National Institutes of Health. The government has certain rights in the invention.--.

Signed and Sealed this
Eighth Day of December, 2020

Andrei Iancu
*Director of the United States Patent and Trademark Office*